(12) United States Patent
Guan et al.

(10) Patent No.: US 11,723,603 B2
(45) Date of Patent: Aug. 15, 2023

(54) SYSTEMS AND METHODS FOR SCANNING AN OBJECT

(71) Applicant: SHANGHAI UNITED IMAGING HEALTHCARE CO., LTD., Shanghai (CN)

(72) Inventors: Xiaolei Guan, Shanghai (CN); Luosheng Zhou, Shanghai (CN); Long Ma, Shanghai (CN); Jianfan Zhou, Shanghai (CN); Bo Li, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 110 days.

(21) Appl. No.: 17/359,691

(22) Filed: Jun. 28, 2021

(65) Prior Publication Data

US 2021/0353232 A1   Nov. 18, 2021

Related U.S. Application Data

(63) Continuation of application No. PCT/CN2019/129390, filed on Dec. 27, 2019.

(30) Foreign Application Priority Data

Dec. 27, 2018   (CN) .......................... 201811614656.7

(51) Int. Cl.
*A61B 5/00* (2006.01)
*G16H 30/40* (2018.01)
(Continued)

(52) U.S. Cl.
CPC ............ *A61B 5/704* (2013.01); *A61B 5/0017* (2013.01); *A61B 5/055* (2013.01); *G01R 33/307* (2013.01);
(Continued)

(58) Field of Classification Search
CPC ....... A61B 5/704; A61B 5/0017; A61B 5/055; A61B 5/0022; A61B 2562/223;
(Continued)

(56) References Cited

U.S. PATENT DOCUMENTS 7,173,426 B1   2/2007 Bulumulla et al.
2008/0143332 A1*  6/2008 Hergt ................. G01R 33/3415
324/318

(Continued)

FOREIGN PATENT DOCUMENTS

CN      103054579 A      4/2013
DE   102007035569 A1     1/2009
(Continued)

OTHER PUBLICATIONS

International Search Report in PCT/CN2019/129390 dated Apr. 7, 2020, 5 pages.
(Continued)

*Primary Examiner* — G. M. A Hyder
(74) *Attorney, Agent, or Firm* — Metis IP LLC

(57) ABSTRACT

A system for scanning an object is provided. The system may include: a supporting table configured to support the object; a first signal conversion unit configured to receive one or more first signals associated with the object and convert the first signals into one or more second signals; and a signal receiver board configured to receive the one or more second signals. The first signal conversion unit may include a plurality of first signal receiving channels. Each first signal receiving channel may be configured to receive a first signal associated with a portion of the object. The supporting table and the signal receiver board may be configured to move relative to each other to cause the signal receiver board to receive at least one second signal corresponding to at least
(Continued)

one first signal received by at least one target channel of the first signal receiving channels.

19 Claims, 9 Drawing Sheets

(51) Int. Cl.
*A61B 5/055* (2006.01)
*G01R 33/30* (2006.01)
*G01R 33/3415* (2006.01)
*G01R 33/36* (2006.01)

(52) U.S. Cl.
CPC ..... *G01R 33/3415* (2013.01); *G01R 33/3621* (2013.01); *G01R 33/3692* (2013.01); *G16H 30/40* (2018.01)

(58) Field of Classification Search
CPC ............. A61B 5/6814; G01R 33/307; G01R 33/3415; G01R 33/3621; G01R 33/3692; G01R 33/56383; G01R 33/3664; G16H 30/40; G16H 20/40
See application file for complete search history.

(56) References Cited

U.S. PATENT DOCUMENTS

| | | | |
|---|---|---|---|
| 2008/0309341 A1* | 12/2008 | Dooms | ............. G01R 33/36 324/318 |
| 2017/0299669 A1 | 10/2017 | Hesels et al. | |
| 2018/0360409 A1 | 12/2018 | Shen et al. | |

FOREIGN PATENT DOCUMENTS

| | | |
|---|---|---|
| JP | H11197133 A | 7/1999 |
| WO | 2006008665 A1 | 1/2006 |
| WO | 2016087272 A | 6/2016 |
| WO | 2020135774 A1 | 7/2020 |

OTHER PUBLICATIONS

Written Opinion in PCT/CN2019/129390 dated Apr. 7, 2020, 5 pages.
First Office Action in Chinese Application No. 201811614656.7 dated May 21, 2020, 13 pages.

* cited by examiner

SYSTEMS AND METHODS FOR SCANNING AN OBJECT

CROSS-REFERENCE TO RELATED APPLICATIONS

This application is a Continuation of International Application No. PCT/CN2019/129390, filed on Dec. 27, 2019, which claims priority to Chinese Patent Application No. 201811614656.7, filed on Dec. 27, 2018, the contents of each of which are incorporated herein by reference in their entirety.

TECHNICAL FIELD

The present disclosure generally relates to a magnetic resonance (MR) system, and in particular, to systems and methods for receiving and transmitting MR signals, and selecting signal receiving channels thereof.

BACKGROUND

An MR apparatus can be used to implement a medical diagnosis and/or treatment for an object (e.g., a patient). One or more signals (e.g., MR signals) associated with the object can be captured by a plurality of signal receiving channels (e.g., radio frequency (RF) signal receiving channels) of the MR apparatus. Because an imaging region in a scanning bore of the MR apparatus is limited in depth, if a scanned part (e.g., a leg) of the object is relatively long, a plurality of scanning operations need to be performed on the scanned part. In each scanning operation, at least one target channel needs to be selected from the plurality of signal receiving channels to capture at least one signal corresponding to a target portion (e.g., a knee) of the scanned part (e.g., the leg) of the object. The selection of the target channel can be realized by using a switch matrix circuit in a signal receiving circuit (e.g., RF receiving coils). However, in some situations, the development of the switch matrix circuit is complicated, thereby costing a large amount of manpower and resources. Besides, the switch matrix circuit can introduce an insertion loss (i.e., a signal attenuation), thereby reducing a signal-noise ratio (SNR) of the entire signal receiving circuit. Therefore, it is desirable to develop systems and methods for selecting signal receiving channels, receiving and transmitting signals efficiently and accurately, and with low cost.

SUMMARY

In one aspect of the present disclosure, a system for scanning an object is provided. The system may include: a supporting table configured to support the object; a first signal conversion unit configured to receive one or more first signals associated with the object and convert the one or more first signals into one or more second signals; and a signal receiver board configured to receive the one or more second signals. The first signal conversion unit may include a plurality of first signal receiving channels. Each channel of the plurality of first signal receiving channels may be configured to receive a first signal associated with a portion of the object. The supporting table and the signal receiver board may be configured to move relative to each other to cause the signal receiver board to receive at least one second signal corresponding to at least one first signal received by at least one target channel of the plurality of first signal receiving channels.

In some embodiments, the system may further include a scanner configured to generate the one or more first signals associated with the object.

In some embodiments, the system may further include a signal processing unit. The signal receiver board may be further configured to transmit the one or more second signals to the signal processing unit. The signal processing unit may be configured to receive the one or more second signals and process the one or more second signals.

In some embodiments, the signal receiver board may be positioned underneath the supporting table.

In some embodiments, the signal receiver board may be positioned in a scanning bore of the scanner.

In some embodiments, the supporting table may include a plurality of signal transmission ports. The signal receiver board may include a plurality of signal receiving ports corresponding to the plurality of signal transmission ports.

In some embodiments, the supporting table and the signal receiver board may be configured to move relative to each other to cause at least one signal transmission port of the plurality of signal transmission ports to be operably coupled to at least one signal receiving port of the plurality of signal receiving ports, such that the at least one second signal is received by the signal receiver board.

In some embodiments, the one or more second signals may be one or more optical signals.

In some embodiments, the first signal conversion unit may be operably coupled to at least one signal transmission port of the plurality of signal transmission ports via a first optical fiber.

In some embodiments, the system may further include a signal processing unit configured to process the one or more second signals. The signal processing unit may be operably coupled to at least one signal receiving port of the plurality of signal receiving ports via a second optical fiber.

In some embodiments, the system may be a magnetic resonance (MR) system, and the one or more first signals may be one or more MR analog signals.

In some embodiments, the plurality of signal transmission ports may be set along a long axis direction of the supporting table.

In some embodiments, at least a portion of the plurality of signal transmission ports may be set close to a long side edge of the supporting table.

In some embodiments, at least a portion of the plurality of signal receiving ports may be set close to a side edge of the signal receiver board. The side edge of the signal receiver board may correspond to the long side edge of the supporting table.

In some embodiments, a signal transmission channel configured to transmit an optical signal of the one or more optical signals may be formed when one of the plurality of signal transmission ports is operably coupled to one of the plurality of signal receiving ports.

In some embodiments, the at least a portion of the plurality of signal transmission ports may be uniformly distributed.

In some embodiments, the at least a portion of the plurality of signal receiving ports may be uniformly distributed.

In some embodiments, a first distance between two adjacent signal transmission ports of the at least a portion of the plurality of signal transmission ports may be the same as a second distance between two adjacent signal receiving ports of the at least a portion of the plurality of signal receiving ports.

In some embodiments, at least one of the plurality of signal transmission ports may include a first opening and a second opening. The first opening may be further away from the signal receiver board than the second opening. A first opening size of the first opening may be larger than a second opening size of the second opening.

In some embodiments, at least one of the plurality of signal receiving ports may include a third opening and a fourth opening. The third opening may be further away from the supporting table than the fourth opening. A third opening size of the third opening may be smaller than a fourth opening size of the fourth opening.

In some embodiments, the system may further include a table control module configured to control the supporting table or the signal receiver board to move.

In some embodiments, the table control module may include a controller, a drive mechanism, and a transmission mechanism. The controller may be set between the signal processing unit and the drive mechanism. The transmission mechanism may be operably connected to the drive mechanism. The controller may be configured to send, when a count of synchronization signal bytes received by the signal processing unit is different from a preset value, a control instruction to the drive mechanism. The drive mechanism may be configured to drive, based on the control instruction, the transmission mechanism to bring the signal receiver board to move relative to the supporting table, or bring the supporting table to move relative to the signal receiver board.

In some embodiments, the first signal conversion unit may include a coil element and an analog signal processing unit. The coil element may be operably coupled to the analog signal processing unit, and may be configured to receive the one or more MR analog signals. The analog signal processing unit may be operably coupled to at least one of the plurality of signal transmission ports via a first optical fiber, and may be configured to receive the one or more MR analog signals and convert the one or more MR analog signals to one or more optical signals.

In some embodiments, the analog signal processing unit may include: an analog-to-digital conversion circuit operably coupled to the coil element, and configured to receive the one or more MR analog signals and convert the one or more MR analog signals to one or more MR digital signals; and a photoelectric conversion circuit set between analog-to-digital conversion circuit and the plurality of signal transmission ports, and configured to convert the one or more MR digital signals to the one or more optical signals, and transmit the one or more optical signals to the at least one of the plurality of signal transmission ports via the first optical fiber.

In another aspect of the present disclosure, a magnetic resonance (MR) apparatus is provided. The apparatus may include: a supporting table; a first signal conversion unit; a signal receiver board; and a signal processing unit. The supporting table may include a plurality of signal transmission ports. The signal receiver board may include a plurality of signal receiving ports corresponding to the plurality of signal transmission ports. The signal receiver board may be positioned underneath the supporting table. The supporting table and the signal receiver board may be configured to move relative to each other to cause at least one signal transmission port of the plurality of signal transmission ports to be aligned with at least one signal receiving port of the plurality of signal receiving ports. The first signal conversion unit may be operably coupled to the at least one signal transmission port via a first optical fiber, and may be configured to receive magnetic resonance (MR) analog signals associated with an object, and convert the MR analog signals to optical signals. The signal processing unit may be operably coupled to the at least one signal receiving port via a second optical fiber, and may be configured to receive the optical signals and process the optical signals.

In another aspect of the present disclosure, a method for determining a signal transmission channel in a system is provided. The method may be implemented on at least one machine each of which has at least one processor and at least one storage device. The method may include: determining a moving direction of a supporting table of the system; and causing the supporting table or a signal receiver board of the system to move relative to each other to make at least one signal transmission port operably coupled to a first signal conversion unit of the system be aligned with at least one signal receiving port to form the signal transmission channel.

In some embodiments, the first signal conversion unit may include a plurality of first signal receiving channels. The at least one signal transmission port operably coupled to the first signal conversion unit may correspond to a target channel of the plurality of first signal receiving channels. The target channel may correspond to a target portion of an object.

In some embodiments, the causing the supporting table or a signal receiver board of the system to move relative to each other may include: causing the supporting table to move relative to the signal receiver board; or causing the signal receiver board to move relative to the supporting table.

In some embodiments, the causing the supporting table or a signal receiver board of the system to move relative to each other may include: causing the signal receiver board to move relative to the supporting table in an initial direction parallel to the moving direction of the supporting table.

In some embodiments, the method may further include: upon the supporting table or the signal receiver board being moved, detecting a count of signal transmission channels that are formed; and comparing the count with a first preset value.

In some embodiments, the method may further include: in response to a determination that the count is less than the first preset value, causing the signal receiver board to move in a first direction or a second direction until the count of signal transmission channels that are formed is equal to the first preset value.

In some embodiments, the method may further include: determining a movement distance of the signal receiver board; comparing the movement distance with a second preset value; and in response to a determination that the movement distance exceeds the second preset value and the count is less than the first preset value, stopping moving the signal receiver board, and providing an alarm.

In some embodiments, the method may further include: causing the signal receiver board to move back by a preset distance.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by another expression if they achieve the same purpose.

Figure 2:
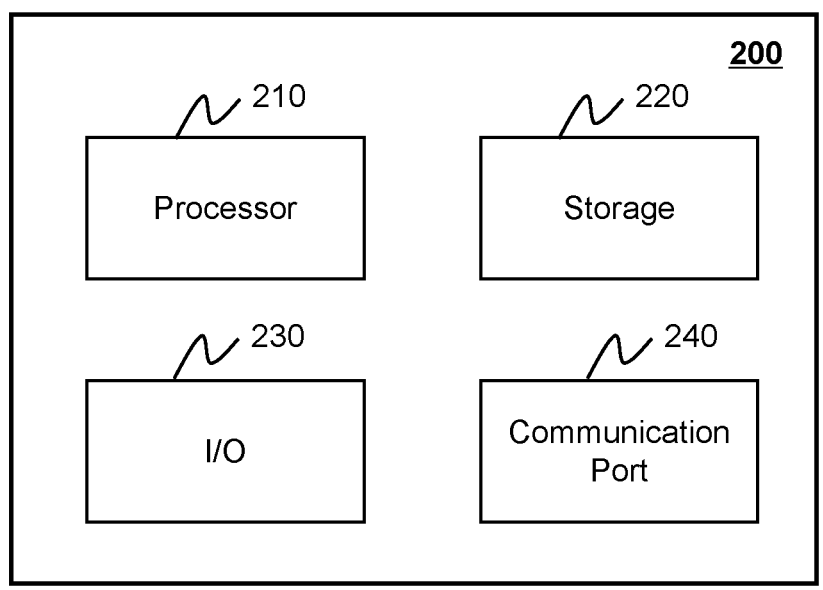
FIG. 2 is a schematic diagram illustrating exemplary hardware and/or software components of an exemplary processing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves and/or may be invoked in response to detected events or interrupts. Software modules/units/blocks configured for execution on computing devices (e.g., processor 210 as illustrated in FIG. 2) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an Erasable Programmable Read Only Memory (EPROM). It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

Provided herein are systems and components for medical imaging and/or medical treatment. In some embodiments, the medical system may include an imaging system. The imaging system may include a single modality imaging system and/or a multi-modality imaging system. The single modality imaging system may include, for example, a magnetic resonance imaging (MRI) system. Exemplary MRI systems may include a superconducting magnetic resonance imaging system, a non-superconducting magnetic resonance imaging system, etc. The multi-modality imaging system may include, for example, a positron emission tomography-magnetic resonance imaging (PET-MRI) system, a single photon emission computed tomography-magnetic resonance imaging (SPECT-MRI) system, a digital subtraction angiography-magnetic resonance imaging (DSA-MRI) system, etc. In some embodiments, the medical system may include a treatment system. The treatment system may include a treatment plan system (TPS), image-guided radiotherapy (IGRT), etc. The image-guided radiotherapy (IGRT) may include a treatment device and an imaging device. The treatment device may include a linear accelerator, a cyclotron, a synchrotron, etc., configured to perform a radiotherapy on a subject. The treatment device may include an accelerator of species of particles including, for example, photons, electrons, protons, or heavy ions. The imaging device may include an MR apparatus, a CT apparatus (e.g., cone beam computed tomography (CBCT) apparatus), a digital radiology (DR) apparatus, an electronic portal imaging device (EPID), etc.

An aspect of the present disclosure relates to systems and methods for scanning an object. The system may include a supporting table, a first signal conversion unit (e.g., an RF receiving and conversion unit), and a signal receiver board. The supporting table may support the object (e.g., a patient). The first signal conversion unit may receive one or more first signals (i.e., RF signals, MR analog signals) associated with the object generated by a scanner (e.g., an MR apparatus). Specifically, the first signal conversion unit may include a plurality of first signal receiving channels. Each channel of the plurality of first signal receiving channels may be configured to receive a first signal associated with a portion of the object. Further, the first signal conversion unit may convert the one or more first signals into one or more second signals (e.g., optical signals). The one or more second signals may be received by the signal receiver board. Specifically, the supporting table and the signal receiver board may move relative to each other to cause the signal receiver board to receive at least one second signal corresponding to at least one first signal received by at least one target channel of the plurality of first signal receiving channels. Further, the signal receiver board may transmit the one or more second signals to a signal processing unit. The signal processing unit may receive the one or more second signals and process the one or more second signals. The one or more processed second signals may be transmitted to a processing device (e.g., the processing device 140) for further processing. For example, the processing device may generate an image (e.g., an MR image) of the object based on the one or more processed second signals.

According to the systems and methods of the present disclosure, a signal transmission channel may be obtained by causing the supporting table or the signal receiver board to move relative to each other, without using a switch matrix circuit, which reduces an operation complexity of channel determination, reduces hardware costs, improves the quality of optical signals transmitted by the channels, and optimizes the workflow of clinical scanning, thereby improving the efficiency and accuracy of imaging.

Figure 1:
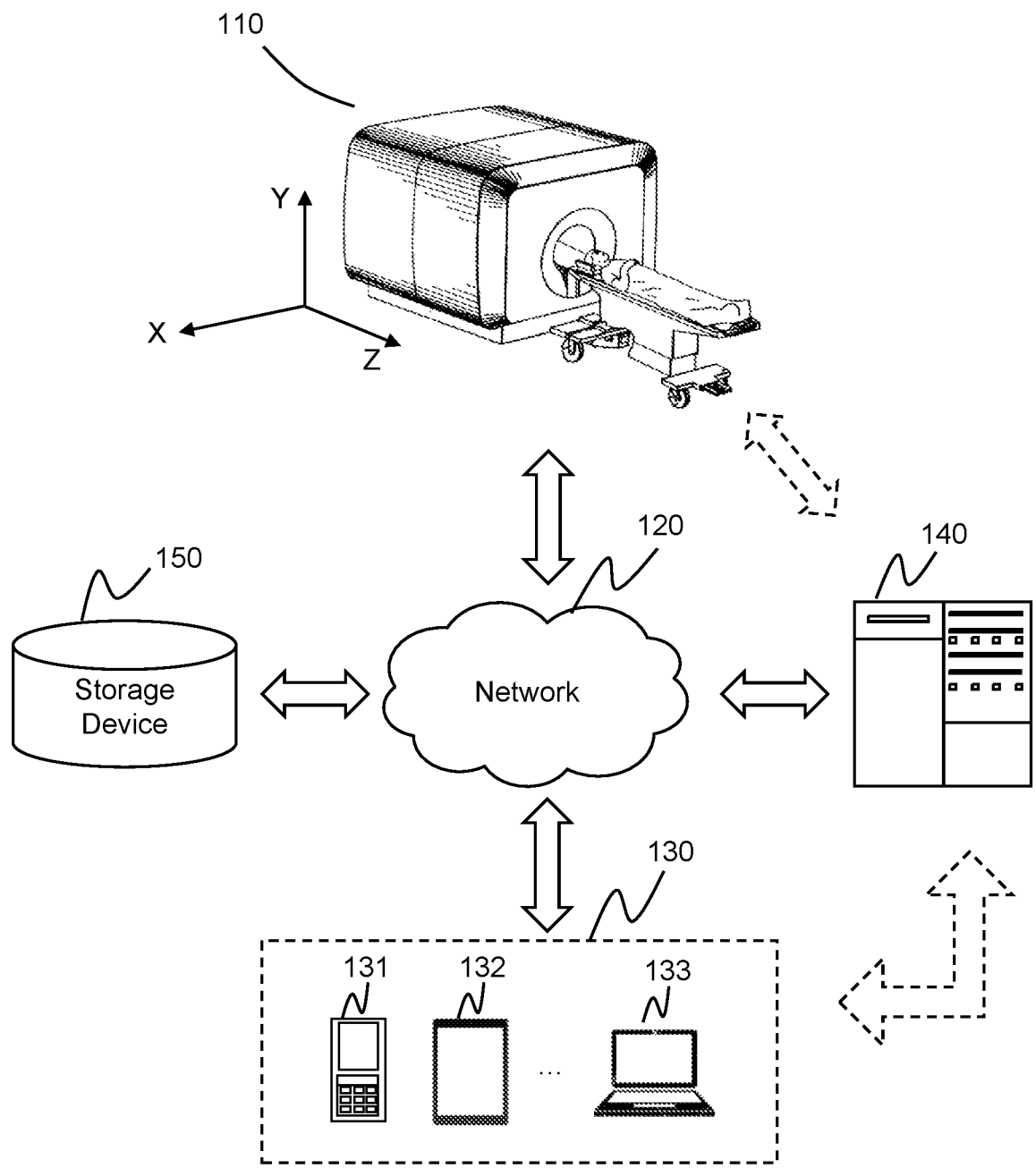
FIG. 1 is a schematic diagram illustrating an exemplary imaging system according to some embodiments of the present disclosure.

FIG. 1 is a schematic diagram illustrating an exemplary imaging system according to some embodiments of the present disclosure. In some embodiments, the imaging system 100 may be a magnetic resonance imaging (MRI) system. As illustrated in FIG. 1, the imaging system 100 may include a scanner 110 (e.g., an MR apparatus), a network 120, one or more terminals 130, a processing device 140, and a storage device 150. The components of the imaging system 100 may be connected in one or more of various ways. Mere by way of example, as illustrated in FIG. 1, the scanner 110 may be connected to the processing device 140 via the network 120. As another example, the scanner 110 may be connected to the processing device 140 directly (as indicated by the bi-directional arrow in dotted lines linking the scanner 110 and the processing device 140). As a further example, the storage device 150 may be connected to the processing device 140 directly or via the network 120. As still a further example, a terminal device (e.g., 131, 132, 133, etc.) may be connected to the processing device 140 directly (as indicated by the bi-directional arrow in dotted lines linking the terminal 130 and the processing device 140) or via the network 120.

The scanner 110 may scan an object located within its detection region (or imaging region) and generate a plurality of data relating to the object. The detection region (or imaging region) of the scanner 110 may be in a scanning bore of the scanner 110. In the present disclosure, "subject" and "object" are used interchangeably. Mere by way of example, the object may include a patient, a man-made object, or the like, or any combination thereof. As another example, the object may include a specific portion, organ, and/or tissue of a patient. As a further example, the object may include a head, a brain, a neck, a body, a shoulder, an arm, a thorax, a heart, a stomach, a blood vessel, a soft tissue, a knee, feet, or the like, or any combination thereof.

In some embodiments, the scanner 110 may be a close-bore MR apparatus or an open-bore MR apparatus. The scanner 110 may include a magnet assembly, a gradient coil assembly, a radiofrequency (RF) coil assembly, and a supporting table, etc. The magnet assembly may generate a main magnetic field for polarizing the object to be scanned. For example, the magnet assembly may include a permanent magnet, a superconducting electromagnet, a resistive electromagnet, etc.

The gradient coil assembly may generate a gradient magnetic field. The gradient coil assembly may generate one or more magnetic field gradient pulses to the main magnetic field in the X direction (Gx), Y direction (Gy), and Z direction (Gz) to encode the spatial information of the subject. As illustrated in FIG. 1, the X-axis, the Y-axis, and the Z-axis may form an orthogonal coordinate system. The X-axis and the Z-axis may be horizontal, and the Y-axis may be vertical. As illustrated in FIG. 1, the positive X direction along the X-axis may be from the right side to the left side of the scanner 110 seen from the direction facing the front of the scanner 110; the positive Y direction along the Y-axis may be from the lower part to the upper part of the scanner 110; the positive Z direction along the Z-axis may refer to a direction in which the object is moved out of the scanning bore of the scanner 110. The detection region may be in the scanning bore. The detection region may be a portion of the scanning bore.

The RF coil assembly may include a plurality of RF coils. The plurality of RF coils may include one or more RF transmitting coils and/or one or more RF receiving coils (e.g., a coil element 4131). The RF transmitting coil(s) may transmit RF pulses to the object. Under the coordinated action of the main magnetic field, the gradient magnetic field, and the RF pulses, MR signals (e.g., MR analog signals) relating to the object may be generated. The RF receiving coils may receive MR signals from the object. In some embodiments, one or more RF coils may both transmit RF pulses and receive MR signals at different times. In some embodiments, the function, size, type, geometry, position, amount, and/or magnitude of the RF coil(s) may be determined or changed according to one or more specific conditions. For example, according to the difference in function and size, the RF coil(s) may be classified as volume coils and local coils. The term "volume coil" as used herein generally refers to coils that are used to provide a homogenous RF excitation field across a relatively large volume, such as to cover the entire body of the object. For example, many commercially available MR apparatuses may include a volume coil that is big enough for whole-body imaging of a human subject, and thus sometimes the volume coil may be referred to as a "body coil." The term "local coil" as used herein may refer to coils that are to be placed in close proximity to a region of interest of the object during MR imaging. The local coils may be designed to achieve improved RF detection sensitivity over a small region of interest (ROI). In some embodiments, the imaging system 100 (e.g., the scanner 110, or the processing device 140) may also include a channel determination module (e.g., the channel determination module 700 illustrated in FIG. 7) configured to determine a signal transmission (or receiving) channel for the MR signals received by the RF receiving coils. More descriptions regarding the scanner 110 may be found elsewhere in the present disclosure (e.g., FIG. 4A and the descriptions thereof).

The network 120 may include any suitable network that can facilitate the exchange of information and/or data for the imaging system 100. In some embodiments, one or more components of the imaging system 100 (e.g., the scanner 110, the terminal 130, the processing device 140, or the storage device 150) may communicate information and/or data with one or more other components of the imaging system 100 via the network 120. For example, the processing device 140 may obtain MR signals (e.g., MR analog signals, optical signals, MR digital signals) associated with the object from the scanner 110 via the network 120. In some embodiments, the network 120 may be any type of wired or wireless network, or a combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the imaging system 100 may be connected to the network 120 to exchange data and/or information.

The terminal 130 may include a mobile device 131, a tablet computer 132, a laptop computer 133, or the like, or any combination thereof. In some embodiments, the mobile device 131 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a smart bracelet, smart footgear, a pair of smart glasses, a smart helmet, a smartwatch, smart clothing, a smart backpack, a smart accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google™ Glass, an Oculus Rift, a Hololens, a Gear VR, etc. In some embodiments, the terminal 130 may remotely operate the scanner 110 and/or the processing device 140. For example, the terminal 130 may remotely operate the scanner 110 to obtain the MR signals associated with the object. In some embodiments, the terminal 130 may operate the scanner 110 and/or the processing device 140 via a wireless connection. In some embodiments, the terminal 130 may receive information and/or instructions inputted by a user and send the received information and/or instructions to the scanner 110 and/or the processing device 140 via the network 120. In some embodiments, the terminal 130 may receive data and/or information from the processing device 140. In some embodiments, the terminal 130 may be part of the processing device 140. In some embodiments, the terminal 130 may be omitted.

The processing device 140 may process data and/or information (e.g., MR signals) obtained from the scanner 110, the terminal 130, and/or the storage device 150. For example, the processing device 140 may obtain MR signals (e.g., MR analog signals, optical signals, MR digital signals) associated with the object from the scanner 110 and generate a scanning image based on the MR signals. In some embodiments, the processing device 140 may be a single server or a server group. The server group may be centralized or distributed. In some embodiments, the processing device 140 may be local or remote. For example, the processing device 140 may access information and/or data stored in or acquired by the scanner 110, the terminal 130, and/or the storage device 150 via the network 120. As another example, the processing device 140 may be directly connected to the scanner 110 (as illustrated by the bidirectional arrow in dashed lines connecting the processing device 140 and the scanner 110 in FIG. 1), the terminal 130 (as illustrated by the bidirectional arrow in dashed lines connecting the processing device 140 and the terminal 130 in FIG. 1), and/or the storage device 150 to access stored or acquired information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 200 having one or more components illustrated in FIG. 2 or a mobile device 300 having one or more components illustrated in FIG. 3 in the present disclosure.

The storage device 150 may store data and/or instructions. In some embodiments, the storage device 150 may store data obtained from the scanner 110, the terminal 130 and/or the processing device 140. In some embodiments, the storage device 150 may store data and/or instructions that the processing device 140 may execute or use to perform exemplary methods described in the present disclosure. For example, the storage device 150 may store data and/or instructions that the processing device 140 may execute to determine a signal transmission channel for the MR signals received by the RF receiving coils of the scanner 110. In some embodiments, the storage device 150 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components of the imaging system 100 (e.g., the scanner 110, the processing device 140, the terminal 130, etc.). One or more components of the imaging system 100 may access the data or instructions stored in the storage device 150 via the network 120. In some embodiments, the storage device 150 may be directly connected to or communicate with one or more components of the imaging system 100 (e.g., the scanner 110, the processing device 140, the terminal 130, etc.). In some embodiments, the storage device 150 may be part of the processing device 140.

In some embodiments, the imaging system 100 may further include one or more power supplies (not shown in FIG. 1) connected to one or more components of the imaging system 100 (e.g., the scanner 110, the processing device 140, the terminal 130, the storage device 150, etc.). It should be noted that the imaging system 100 and the scanner 110 illustrated in FIG. 1 are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

FIG. 2 is a schematic diagram illustrating exemplary hardware and/or software components of an exemplary processing device according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the processing device 140 in accordance with techniques described herein. The computer instructions may include routines, programs, objects, components, signals, data structures, procedures, modules, and functions, which perform particular functions described herein. For example, the processor 210 may process data obtained from the scanner 110, the terminal 130, the storage device 150, and/or any other component (e.g., the channel determination module) of the imaging system 100. In some embodiments, the processor 210 may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration purposes, only one processor is described in the computing device 200. However, it should be noted that the computing device 200 in the present disclosure may also include multiple processors, and thus operations of a method that are performed by one processor as described in the present disclosure may also be jointly or separately performed by the multiple processors. For example, if in the present disclosure the processor of the computing device 200 executes both operations A and B, it should be understood that operations A and step B may also be performed by two different processors jointly or separately in the computing device 200 (e.g., a first processor executes operation A and a second processor executes operation B, or the first and second processors jointly execute operations A and B).

The storage 220 may store data/information obtained from the scanner 110, the terminal 130, the storage device 150, or any other component (e.g., the channel determination module) of the imaging system 100. In some embodiments, the storage 220 may include a mass storage device, a removable storage device, a volatile read-and-write memory, a read-only memory (ROM), or the like, or any combination thereof. For example, the mass storage device may include a magnetic disk, an optical disk, a solid-state drive, etc. The removable storage device may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure.

The I/O 230 may input or output signals (e.g., MR signals), data, or information. In some embodiments, the I/O 230 may enable user interaction with the processing device 140. In some embodiments, the I/O 230 may include an input device and an output device. Exemplary input devices may include a keyboard, a mouse, a touch screen, a microphone, a trackball, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

Merely by way of example, a user (e.g., an operator) may input data related to an object (e.g., a patient) that is being/to be imaged/scanned (or treated) through the I/O 230. The data related to the object may include identification information (e.g., the name, age, gender, medical history, contact information, physical examination result, etc.) and/or the test information including the nature of the scan that must be performed. The user may also input parameters needed for the operation of the scanner 110, such as image contrast and/or ratio, a region of interest (ROI), slice thickness, an imaging type (e.g., T1 weighted imaging, T2 weighted imaging, proton density weighted imaging, etc.), T1, T2, an echo type (spin echo, fast spin echo (FSE), fast recovery FSE, single shot FSE, gradient recalled echo, fast imaging with steady-state precession, and so on), a flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), a scan type, a type of sampling, or the like, or any combination thereof. The I/O 230 may also display MR images generated based on sampled data.

The communication port 240 may be connected to a network (e.g., the network 120) to facilitate data communications. The communication port 240 may establish connections between the processing device 140 and the scanner 110, the terminal 130, or the storage device 150. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
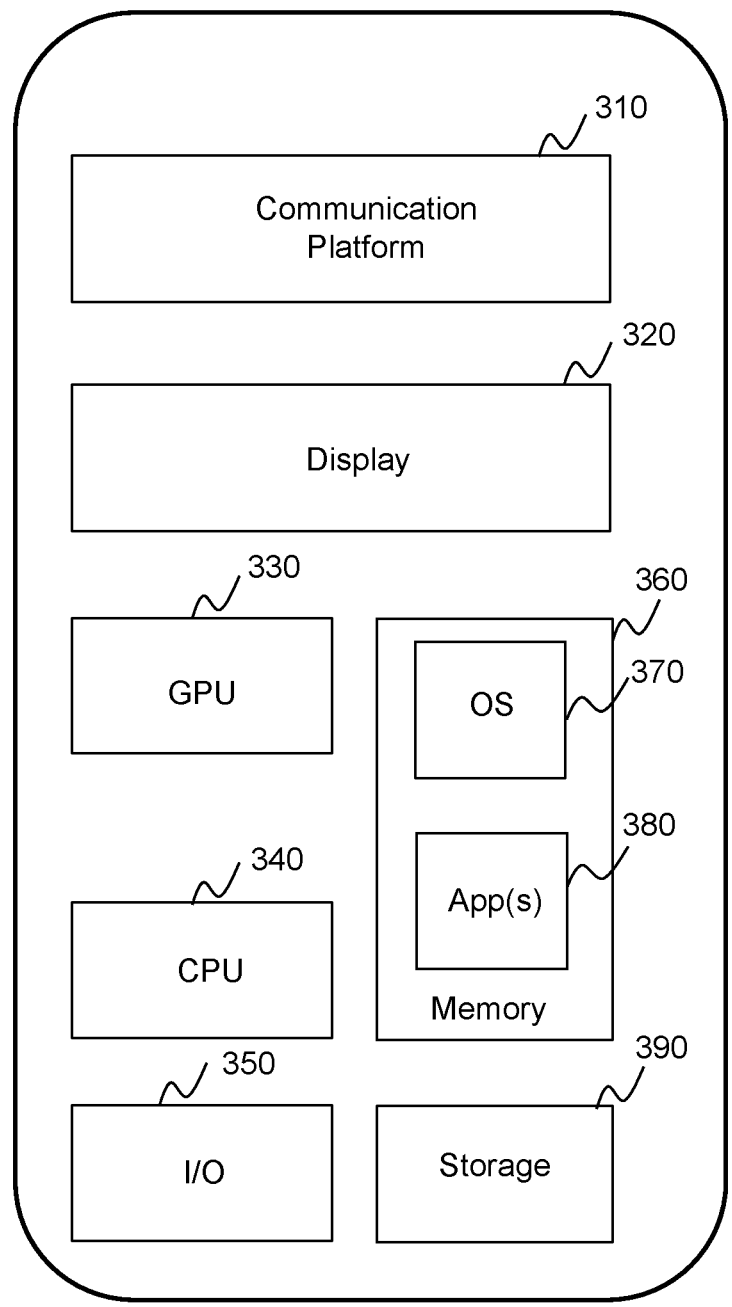
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, Harmony OS, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the imaging system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate and track shapes of a target as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result the drawings should be self-explanatory.

Figure 4A:
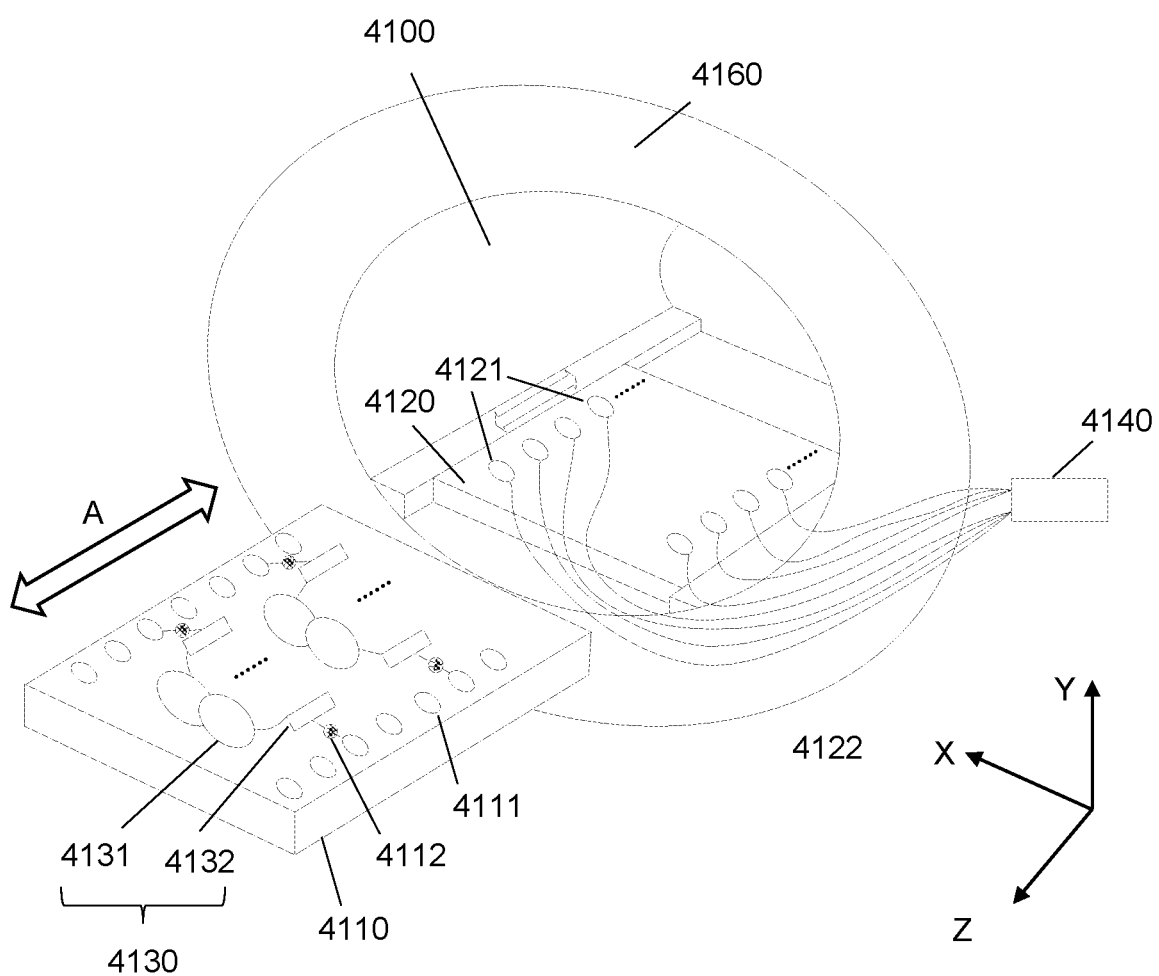
FIG. 4A is a schematic diagram illustrating an exemplary MR apparatus according to some embodiments of the present disclosure.

FIG. 4A is a schematic diagram illustrating an exemplary MR apparatus according to some embodiments of the present disclosure. As illustrated in FIG. 4A, the MR apparatus 400 may include a supporting table 4110, a signal receiver board 4120, one or more first signal conversion units 4130 (also referred to as "RF receiving and conversion units"), and a signal processing unit 4140. In some embodiments, the one or more first signal conversion units 4130 may be referred to as a first signal conversion assembly.

The MR apparatus 400 may be an example of the scanner 110. In some embodiments, the MR apparatus 400 may include a gantry 4160. The gantry 4160 may include a scanning bore 4100 configured to accommodate the supporting table 4110 and a scanned object (not shown). In some embodiments, the supporting table 4110 may be configured to support the scanned object (e.g., a patient). For example, the scanned object may lie on the supporting table 4110. The supporting table 4110 supporting the scanned object may be moved to an imaging region (not shown) in the scanning bore 4100 of the gantry 4160. In some embodiments, the MR apparatus 400 (e.g., an RF coil assembly thereof) may generate one or more signals (e.g., MR analog signals, RF signals) associated with the scanned object and transmit the signal(s) to the signal processing unit 4140.

The first signal conversion unit(s) 4130 may be configured to receive the one or more first signals associated with the object (or a portion (e.g., a region of interest (ROI)) of the object). In some embodiments, the first signal conversion unit(s) 4130 may convert the received first signal(s) into one or more second signals (e.g., optical signals). In some embodiments, the first signal conversion unit(s) 4130 may be operably coupled to (e.g., plugged into) or integrated into the supporting table 4110. In some embodiments, each first signal conversion unit 4130 may include one or more coil elements 4131 and an analog signal processing unit 4132. The coil element(s) 4131 may be operably coupled to (e.g., electrically connected to) the analog signal processing unit 4132, and be configured to receive the first signal(s) (e.g., MR analog signal(s)). In some embodiments, the coil element(s) 4131 may transmit the received first signal(s) to the analog signal processing unit 4132. The analog signal processing unit 4132 may be configured to receive the first signal(s) and/or convert the first signal(s) to one or more second signals (e.g., optical signals). In some embodiments, one coil element 4131 may include one or more coils (e.g., RF receiving coils). The coil(s) in a same coil element 4131 may correspond to a same analog signal processing unit 4132 (i.e., the first signal(s) received in each of the coil(s) in the same coil element 4131 can be transmitted to the same analog signal processing unit 4132 that is operably coupled to the coil element 4131). In some embodiments, the coil elements 4131 in a same first signal conversion unit 4130 may correspond to a same analog signal processing unit 4132. More descriptions of the correspondence of the coil elements 4131 and the analog signal processing unit 4132 may be found elsewhere in the present disclosure (e.g., FIG. 4B and descriptions thereof).

In some embodiments, the supporting table 4110 may be equipped with a plurality of signal transmission ports (also referred to as "optical fiber transmission ports") 4111. In some embodiments, at least one first signal conversion unit 4130 may be operably coupled (e.g., optically coupled) to at least one signal transmission port 4111 via a first optical fiber 4112. For example, the analog signal processing unit 4132 in the at least one first signal conversion unit 4130 may be operably coupled to the at least one signal transmission port 4111 via the first optical fiber 4112. In some embodiments, the analog signal processing unit 4132 may output the second signal(s) to the signal receiver board 4120 via the first optical fiber 4112 and the signal transmission port 4111.

In some embodiments, the signal receiver board 4120 may be configured to receive the second signal(s). In some embodiments, the signal receiver board 4120 may be equipped with a plurality of signal receiving ports (also referred to as "optical fiber receiving ports") 4121 corresponding to the plurality of signal transmission ports 4111. In some embodiments, the signal receiving port 4121 may need to be operably coupled to the signal transmission port 4111 to transmit signal(s) from the first signal conversion unit 4130 to the signal receiver board 4120. In some embodiments, when a signal transmission port 4111 is operably coupled to a signal receiving port 4121, the signal transmission port 4111 may be considered to correspond to the signal receiving port 4121. In some embodiments, each signal transmission port 4111 that are transmitting signal(s) may have a corresponding signal receiving port 4121.

In some embodiments, the supporting table 4110 may be positioned outside the scanning bore 4100 or inside the scanning bore 4100. In some embodiments, a portion of the supporting table 4110 may be positioned outside the scanning bore 4100, while a portion of the supporting table 4110 may be positioned inside the scanning bore 4100. In some embodiments, the supporting table 4110 may be caused to move from the outside of the scanning bore 4100 to the inside of the scanning bore 4100, or from the inside of the scanning bore 4100 to the outside of the scanning bore 4100, along a long axis direction (i.e., the Z-axis direction as indicated by the arrow A in FIG. 4A) of the supporting table 4110. In some embodiments, the supporting table 4110 may move left or right along a short axis direction (e.g., the X-axis direction) of the supporting table 4110. In some embodiments, when the supporting table 4110 is located inside the scanning bore 4100, the signal receiver board 4120 may be positioned underneath the supporting table 4110. In some embodiments, the signal receiver board 4120 may be positioned inside the scanning bore 4100. In some embodiments, the signal receiver board 4120 may move only inside the scanning bore 4100. In some embodiments, a position of the signal receiver board 4120 may be adjusted slightly back or forth along the long axis direction (e.g., as indicated by the arrow A in FIG. 4A) of the supporting table 4110. In some embodiments, the position of the signal receiver board 4120 may be adjusted slightly left or right along the short axis direction (i.e., a direction perpendicular to the long axis direction) of the supporting table 4110. In some embodiments, the supporting table 4110 and the signal receiver board 4120 may be configured to move relative to each other to cause at least one signal transmission port 4111 to be operably coupled (e.g., optically coupled) to at least one signal receiving port 4121. In some embodiments, a signal transmission port 4111 being operably coupled to a signal receiving port 4121 may refer that the signal transmission port 4111 is aligned with the signal receiving port 4121 such that second signal(s) (e.g., optical signal(s)) can be successfully and stably transmitted from the signal transmission port 4111 to the signal receiving port 4121.

In some embodiments, the signal processing unit 4140 may be operably coupled to the signal receiver board 4120. In some embodiments, the signal receiver board 4120 may transmit the second signal(s) to the signal processing unit 4140. In some embodiments, the signal processing unit 4140 may be operably coupled to the signal receiving port(s) 4121 of the signal receiver board 4120 via one or more second optical fibers 4122. The signal processing unit 4140 may be configured to receive the second signal(s) from the signal receiver board 4120 via the second optical fiber(s) 4122 and/or further process the second signal(s). In some embodiments, the second signal(s) may be digital signal(s) (e.g., optical signals), and the signal processing unit 4140 may be a digital signal processing unit.

In some embodiments, the first signal conversion assembly may include a plurality of first signal receiving channels. For example, each first signal conversion unit 4130 may be referred to as a first signal receiving channel. Alternatively, in some embodiments, one first signal conversion unit 4130 may include one or more first signal receiving channels. Each channel of the first signal receiving channel(s) may be configured to receive a first signal associated a portion of the object. As used herein, one first signal receiving channel may correspond to one coil element 4131. In some embodiments, one or more of the first signal conversion unit(s) 4130 (or a portion thereof) may be worn on the object (or a portion of the object). For example, a coil element for receiving first signal(s) associated with a leg, an arm, a neck, etc., of the object may be worn on the corresponding portion of the object. In some embodiments, one first signal receiving channel may refer to one channel formed by a coil element 4131 and a corresponding analog signal processing unit 4132. For example, if a first signal conversion unit 4130 includes 24 first signal receiving channels, and 4 adjacent coil elements correspond to one analog signal processing unit 4132, then the first signal conversion unit 4130 may have 6 analog signal processing units 4132, and the converted signals (e.g., the second signal(s)) can be output by the 6 analog signal processing units 4132 via 6 optical fibers (e.g., first optical fibers), respectively.

In some embodiments, each first signal conversion unit 4130 may be fixedly connected to one of a plurality of first optical fibers 4112. In some embodiments, one signal transmission port 4111 may be selected from the plurality of signal transmission ports 4111 to be operably coupled to the first optical fiber 4112 connected to a first signal conversion unit 4130 (e.g., by inserting the first optical fiber 4112 into the selected signal transmission port 4111), such that the second signal(s) may be transmitted to the selected signal transmission port 4111 from the first signal conversion unit 4130 via the first optical fiber 4112. In some embodiments, due to a length limitation of the first optical fiber 4112, the signal transmission port 4111 may be selected based on a distance between the signal transmission port 4111 and the first optical fiber 4112. For example, the signal transmission port 4111 close to the first optical fiber 4112 may be selected to be operably coupled to the first optical fiber 4112. In some embodiments, when a portion (e.g., a foot) of the object needs to be scanned, the first signal conversion unit 4130 coupled to the foot of the object may receive signal(s) associated with the foot of the object, and a signal transmission port 4111 close to the foot of the object may be selected to be operably coupled to the first optical fiber 4112. The above process can be considered as a process of channel selection.

In some embodiments, the operable coupling between the first optical fiber 4112 and the signal transmission port 4111 may be performed manually. For example, the operable coupling may be performed by an operator by inserting the first optical fiber 4112 into the selected signal transmission port 4111. In some embodiments, the operable coupling between the first optical fiber 4112 and the signal transmission port 4111 may be performed automatically. For example, each first optical fiber 4112 may be operably coupled to a corresponding signal transmission port 4111, but a switch (e.g., an optical baffle) may be set between the first optical fiber 4112 and the corresponding signal transmission port 4111. In some embodiments, the processing device 140 may automatically control an on/off state of the signal transmission channel (formed by the first optical fiber 4112, the corresponding signal transmission port 4111, etc.) by controlling an on/off state of the switch set between the first optical fiber 4112 and the corresponding signal transmission port 4111. When a first signal conversion unit 4130 coupled to a target portion of the object is used to receive signal(s) associated with the target portion of the object, the first optical fiber 4112 connected to the first signal conversion unit 4130 may be used to transmit signal(s), and the switch between the first optical fiber 4112 and the corresponding signal transmission port 4111 may be turned on to allow signal transmission.

In some embodiments, a first signal conversion unit 4130 (or a coil element thereof) corresponding to the target portion of the object may be referred to as a target channel. For example, if the target portion (e.g., a neck) of the object is scanned, a coil element 4131 may be worn on the neck of the object, the target channel may refer to a first signal conversion unit 4130 including the coil element 4131. In some embodiments, after the target channel is operably coupled to a signal transmission port 4111 via the first optical fiber 4112, the supporting table 4110 and/or the signal receiver board 4120 may be caused to move relative to each other to cause the signal transmission port 4111 to be operably coupled (e.g., optically coupled) to a corresponding signal receiving port 4121, such that a second signal corresponding to the first signal received by the target channel (of the plurality of first signal receiving channels) is received by the signal receiver board 4120. In some embodiments, when a plurality of target channels are operably coupled to a plurality of signal transmission ports 4111, the supporting table 4110 and/or the signal receiver board 4120 may be caused to move relative to each other to cause each of the plurality of signal transmission ports 4111 to be operably coupled to a corresponding signal receiving port 4121.

In some embodiments, a signal transmission channel configured to transmit second signal(s) (e.g., optical signal(s)) may be formed when one signal transmission port 4111 is operably coupled to one signal receiving port 4121. Specifically, when one signal transmission port 4111 is operably coupled to (e.g., aligned with) one signal receiving port 4121, the optical signal(s) output from a corresponding analog signal processing units 4132 may be transmitted to the signal transmission port 4111 via the first optical fiber 4112, and further transmitted to the signal receiving port 4121 operably coupled to the signal transmission port 4111. Further, the optical signal(s) may be transmitted via the second optical fiber 4122 to the signal processing unit 4140 for further processing. In some embodiments, because multimode fibers have a large transmission bandwidth and an ability to transmit multimode lights, the first optical fiber(s) 4112 and/or the second optical fiber(s) 4122 may be implemented in a configuration of multimode fibers to improve transmission efficiency of the optical signal(s). In some embodiments, each signal receiving port 4121 may be fixedly connected to one second optical fiber 4122, and the number (or count) of the signal receiving ports 4121 may be equal to the number (or count) of the second optical fibers 4122. In some embodiments, each signal receiving port 4121 may be operably coupled (e.g., plug connection) to one second optical fiber 4122 when needed, and the number (or count) of the signal receiving ports 4121 may be greater than the number (or count) of the second optical fibers 4122.

Figure 4B:
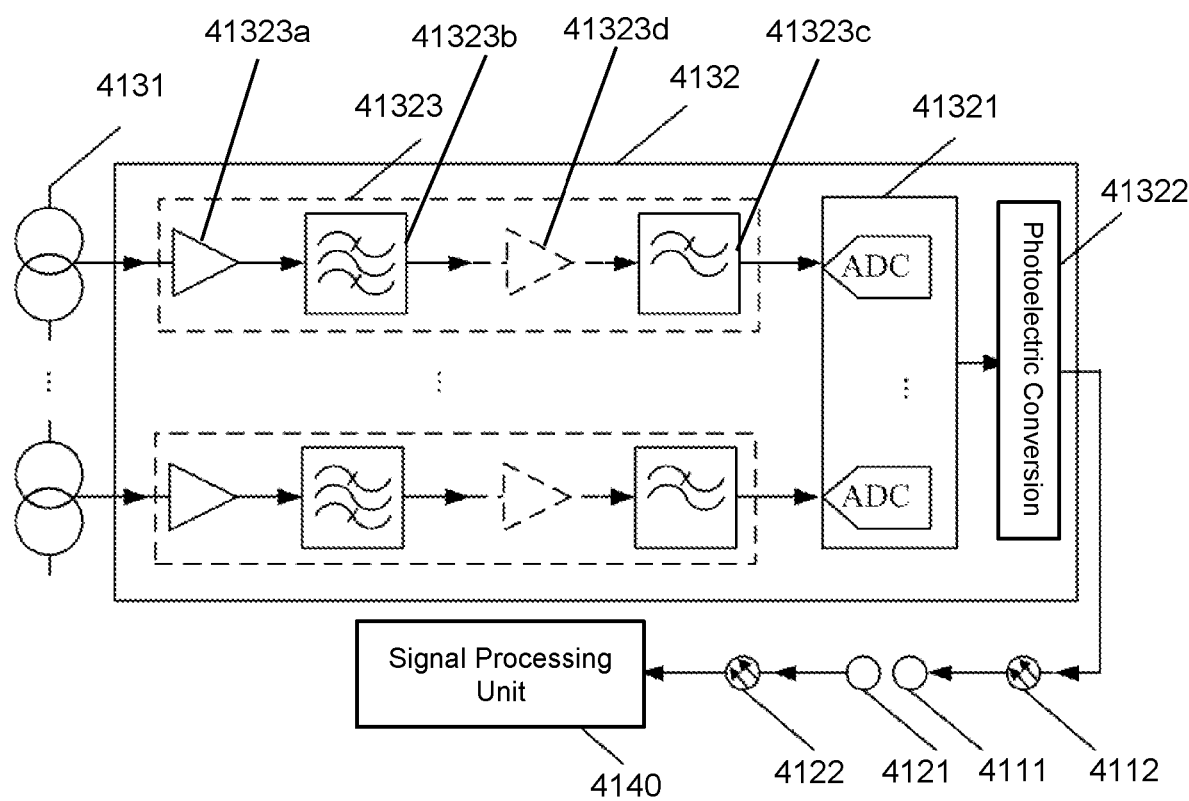
FIG. 4B is a schematic diagram illustrating an exemplary signal transmission channel according to some embodiments of the present disclosure.

FIG. 4B is a schematic diagram illustrating an exemplary signal transmission channel according to some embodiments of the present disclosure. The signal transmission channel may include one or more coil elements 4131, an analog signal processing unit 4132, a first optical fiber 4112, a signal transmission port 4111, a signal receiving port 4121, and a second optical fiber 4122. Signal(s) may be transmitted through the signal transmission channel to the signal processing unit 4140. The analog signal processing unit 4132 may include one or more analog-to-digital (AD) conversion circuits 41321 and a photoelectric conversion circuit 41322. In some embodiments, the analog signal processing unit 4132 may further include one or more amplifying circuits 41323 (e.g., filer amplifying circuits).

In some embodiments, each AD conversion circuit 41321 may be operably coupled (e.g., electrically connected) to one coil element 4131. In some embodiments, each AD conversion circuit 41321 may be configured to receive one or more MR analog signals from the coupled coil element 4131, and/or convert the MR analog signal(s) to one or more MR digital signals.

In some embodiments, the photoelectric conversion circuit 41322 may be set between the AD conversion circuits 41321 and the signal transmission port 4111. In some embodiments, the photoelectric conversion circuit 41322 may be configured to convert the MR digital signal(s) to one or more optical signals, and/or transmit the optical signal(s) to the signal transmission port 4111 via the first optical fiber 4112.

In some embodiments, in order to improve the transmission efficiency of signals, before the MR analog signal(s) are converted to the MR digital signal(s), one or more amplifying circuits 41323 may be set between the AD conversion circuit(s) 41321 and the coil element(s) 4131 to perform an amplification (e.g., a filter amplification) on the MR analog signal(s). In some embodiments, one amplifying circuit 41323 may be set between one AD conversion circuit 41321 and a corresponding coil element 4131. In some embodiments, each amplifying circuit 41323 may include a main amplifier 41323$a$, a bandpass filter 41323$b$, and/or a low pass filter 41323$c$. The main amplifier 41323$a$ may be configured to receive the MR analog signal(s) transmitted from a corresponding coil element 4131, and/or perform a power amplification on the MR analog signal(s). The amplified MR analog signal(s) may be transmitted to the bandpass filter 41323$b$. The bandpass filter 41323$b$ may be configured to denoise the amplified MR analog signal(s). The denoised MR analog signal(s) may be transmitted to the low pass filter 41323$c$. The low pass filter 41323$c$ may be configured to process the denoised MR analog signal(s) to reduce aliasing of the denoised MR analog signal(s). In some embodiments, the main amplifier 41323$a$ may be a low noise amplifier. In some embodiments, each amplifying circuit 41323 may further include a secondary amplifier 41323$d$. The secondary amplifier 41323$d$ may be set between the bandpass filter 41323$b$ and the low pass filter 41323$c$. The secondary amplifier 41323$d$ may be configured to perform a power amplification on the denoised MR analog signal(s) received from the bandpass filter 41323$b$, and/or transmit the amplified MR analog signal(s) to the low pass filter 41323$c$. It should be noted that the amplifying circuit(s) 41323 illustrated in FIG. 4B are merely provided for the purposes of illustration, and not intended to limit the scope of the present disclosure. For example, one or more of the amplifying circuit(s) 41323 may be omitted.

Specifically, after receiving the MR analog signal(s), the coil element 4131 may transmit the MR analog signal(s) to a corresponding amplifying circuit 41323. The corresponding amplifying circuit 41323 may preprocess (e.g., amplify, filter, denoise, etc.) the MR analog signal(s), and/or transmit the preprocessed MR analog signal(s) to a corresponding AD conversion circuit 41321. The corresponding AD conversion circuit 41321 may convert the preprocessed MR analog signal(s) to one or more MR digital signals, and/or transmit the MR digital signal(s) to the photoelectric conversion circuit 41322. The photoelectric conversion circuit 41322 may convert the MR digital signal(s) to one or more optical signals, and/or transmit the optical signal(s) to the signal transmission port 4111 via the first optical fiber 4112. The optical signal(s) may be transmitted to the signal receiving port 4121 operably coupled to the signal transmission port 4111. Further, the optical signal(s) may be transmitted to the signal processing unit 4140 via the second optical fiber 4122. The signal processing unit 4140 may perform a signal processing operation (e.g., a carrier modulation, a decimation filtering, etc.) on the optical signal(s), and/or transmit the processed optical signal(s) to a processing device (e.g., the processing device 140) for further processing (e.g., generating a scanning image based on the MR signals).

It should be noted that a position of the signal processing unit 4140 is not intended to be limiting. In some embodiments, the signal processing unit 4140 may be positioned in a scanning room that accommodates the scanner 110. For example, the signal processing unit 4140 may be positioned inside the scanner 110 (e.g., a scanning bore of the scanner).

As another example, the signal processing unit 4140 may be positioned outside the scanner 110 (e.g., a certain distance away from the scanner 110), such that the signal processing unit 4140 cause no electromagnetic interference(s) to the scanner 110, and/or the magnetic field generated by the scanner 110 does not affect the normal operation of the signal processing unit 4140. In some embodiments, the signal processing unit 4140 may be positioned in an equipment room that accommodates the processing device 140, the storage device 150, and/or the terminal(s) 130. For example, the signal processing unit 4140 may be integrated into or be part of the processing device 140.

In some embodiments, the signal receiver board 4120 may be positioned underneath the supporting table 4110 (i.e., the signal receiver board 4120 and the object lying on the supporting table 4110 may face opposite surfaces of the supporting table 4110). In some embodiments, the signal receiver board 4120 may be positioned in the scanning bore 4100 of the gantry 4160. In some embodiments, when the supporting table 4110 is located inside the scanning bore 4100, the supporting table 4110 may be located directly above the signal receiver board 4120, and may at least partially overlap with the signal receiver board 4120 (e.g., as illustrated in FIG. 4D). For example, the supporting table 4110 may cover the signal receiver board 4120. In some embodiments, when the supporting table 4110 is located outside the scanning bore 4100, at least a portion of the supporting table 4110 may not overlap with the signal receiver board 4120. However, a height (e.g., in the Y-axis direction shown in FIG. 1) of a lower surface of the supporting table 4110 may be higher than a height (e.g., in the Y-axis direction shown in FIG. 1) of an upper surface of the signal receiver board 4120. In some embodiments, the signal receiver board 4120 may be set adjacent to the supporting table 4110 in a vertical direction (e.g., in the Y-axis direction shown in FIG. 1), such that the supporting table 4110 and the signal receiver board 4120 can move relative to each other without rubbing each other.

In the present disclosure, the supporting table 4110 may include a plurality of signal transmission ports 4111, and the signal receiver board 4120 may include a plurality of signal receiving ports 4121 corresponding to the plurality of signal transmission ports 4111. The signal receiver board 4120 may be positioned in the scanning bore 4100 of the MR apparatus 400, and underneath the supporting table 4110. The supporting table 4110 and the signal receiver board 4120 may be configured to move relative to each other to cause at least one signal transmission port of the plurality of signal transmission ports 4111 to be aligned with at least one signal receiving port of the plurality of signal receiving ports 4121. The first signal conversion unit 4130 may be operably coupled to the at least one signal transmission port 4111 via a first optical fiber 4112, and may be configured to receive MR analog signals associated with an object, and/or convert the MR analog signals to optical signals. The signal processing unit 4140 may be operably coupled to the at least one signal receiving port 4121 via a second optical fiber 4122, and may be configured to receive the optical signals, and/or process the optical signals. A signal transmission channel configured to transmit optical signal(s) may be formed when one of the plurality of signal transmission ports 4111 is operably coupled to one of the plurality of signal receiving ports 4121.

According to the systems and methods illustrated above, with the configuration of the signal transmission port(s) 4111 and corresponding signal receiving port(s) 4121, the first optical fiber(s) 4112 optically connected to the signal transmission port(s) 4111 may be operably coupled to the second optical fiber(s) 4122 optically connected to the signal receiving port(s) 4121 by aligning the signal transmission port(s) 4111 with corresponding signal receiving port(s) 4121, and accordingly signal transmission channel(s) can be formed to realize the transmission of optical signal(s). The signal transmission channel(s) can be formed (adjusted, or selected) by mechanically aligning the signal transmission port(s) 4111 with corresponding signal receiving port(s) 4121, and the selection of the signal transmission channel(s) can be realized by moving the supporting table 4110 without using an instruction for the selection of the signal transmission channel(s) via software control, thereby reducing the time for preparing imaging and improving efficiency. Therefore, an inconvenience of channel selection using a switch matrix circuit can be reduced or eliminated, an operation complexity of channel selection can be reduced, hardware cost can be reduced, the quality of optical signals transmitted by the channel can be improved, the imaging workflow can be optimized, and the efficiency and accuracy of imaging can be improved.

In some embodiments, a signal transmission channel may be formed based on at least one signal transmission port 4111 and at least one signal receiving port 4121 corresponding to (or operably coupled to) the signal transmission port 4111. In some embodiments, in order to ensure the number (or count) of the signal transmission ports 4111 without affecting the normal use of the MR apparatus 400, the plurality of signal transmission ports 4111 may be set along a long axis direction (e.g., as indicated by the arrow A in FIG. 4A) of the supporting table 4110. For example, one or more rows of signal transmission ports 4111 may be set along the long axis direction of the supporting table 4110. In some embodiments, at least a portion of the plurality of signal transmission ports 4111 may be set close to a long side edge of the supporting table 4110. For example, as illustrated in FIG. 4A, each long side edge of the supporting table 4110 may be equipped with a row of signal transmission ports 4111. In some embodiments, the signal transmission port(s) 4111 may be set a certain distance (e.g., a relatively small distance (e.g., 0-20 cm)) away from the long side edge of the supporting table 4110. In some embodiments, the signal transmission port(s) 4111 may be set on the long side edge of the supporting table 4110. In some embodiments, at least a portion of the plurality of signal receiving ports 4121 may be set close to a side edge (corresponding to the long side edge of the supporting table 4110) of the signal receiver board 4120. For example, if the left-side edge (seen from the direction facing the front of the scanner 110) of the supporting table 4110 is equipped with signal transmission ports 4111, then the left-side edge of the signal receiver board 4120 may be equipped with corresponding signal receiving ports 4121. As another example, if the right-side edge (seen from the direction facing the front of the scanner 110) of the supporting table 4110 is equipped with signal transmission ports 4111, then the right-side edge of the signal receiver board 4120 may be equipped with corresponding signal receiving ports 4121.

In some embodiments, the plurality of signal transmission ports 4111 may be configured as a hole structure that penetrates through an upper surface and a lower surface of the supporting table 4110. Accordingly, the corresponding signal receiving ports 4121 may be configured as a hole structure that penetrates an upper surface and a lower surface of the signal receiver board 4120. In some embodiments, the signal transmission ports 4111 may be configured as a hole structure formed by a side surface and the lower surface of the supporting table 4110. Accordingly, the corresponding signal receiving ports 4121 may be configured as a hole structure formed by an upper surface and a side surface of the signal receiver board 4120. In some embodiments, the hole structure(s) of the signal transmission ports 4111 and/or the signal receiving ports 4121 may include a linear structure and/or a nonlinear structure. The linear hole structure may refer to a hole structure extending in a straight line without an inflection point. The nonlinear hole structure may refer to a hole structure that does not extend in a straight line. When one of the plurality of signal transmission ports 4111 is operably coupled to (e.g., aligned with) one of the plurality of signal receiving ports 4121, a signal transmission channel may be formed to transmit optical signal(s) from the first optical fiber 4112 to the second optical fiber 4122.

It should be noted that when a hole structure of the signal transmission ports 4111 and/or the signal receiving ports 4121 is a nonlinear structure, a light-guiding structure may be set in the hole structure to change a transmission direction of the optical signal(s), such that the optical signal(s) in the first optical fiber 4112 can be successfully transmitted to the second optical fiber 4122 via the signal transmission port 4111 and the signal receiving port 4121. Exemplary light-guiding structures may include a lens, a refractor, a reflector, a mirror, or the like, or any combination thereof.

In some embodiments, in order to improve the coupling extent between the plurality of signal transmission ports 4111 set in the supporting table 4110 and the corresponding signal receiving ports 4121 set in the signal receiver board 4120, at least a portion of the plurality of signal transmission ports 4111 and at least a portion of the plurality of signal receiving ports 4121 may be uniformly distributed (e.g., close to the side edge(s) of the supporting table 4110 and the side edge(s) of the signal receiver board 4120 on the same side, respectively). In some embodiments, a first distance between two adjacent signal transmission ports 4111 of the at least a portion of the plurality of signal transmission ports 4111 and a second distance between two adjacent signal receiving ports 4121 of the at least a portion of the plurality of signal receiving ports 4121 may have an association relationship. In some embodiments, the association relationship may be that the first distance is a preset multiple of the second distance. In some embodiments, the preset multiple may be 1, i.e., the first distance between two adjacent signal transmission ports 4111 close to a side edge of the supporting table 4110 is the same as a second distance between two adjacent signal receiving ports 4121 close to a side edge (of a same side of the supporting table) of the signal receiver board 4120.

Figure 4C:
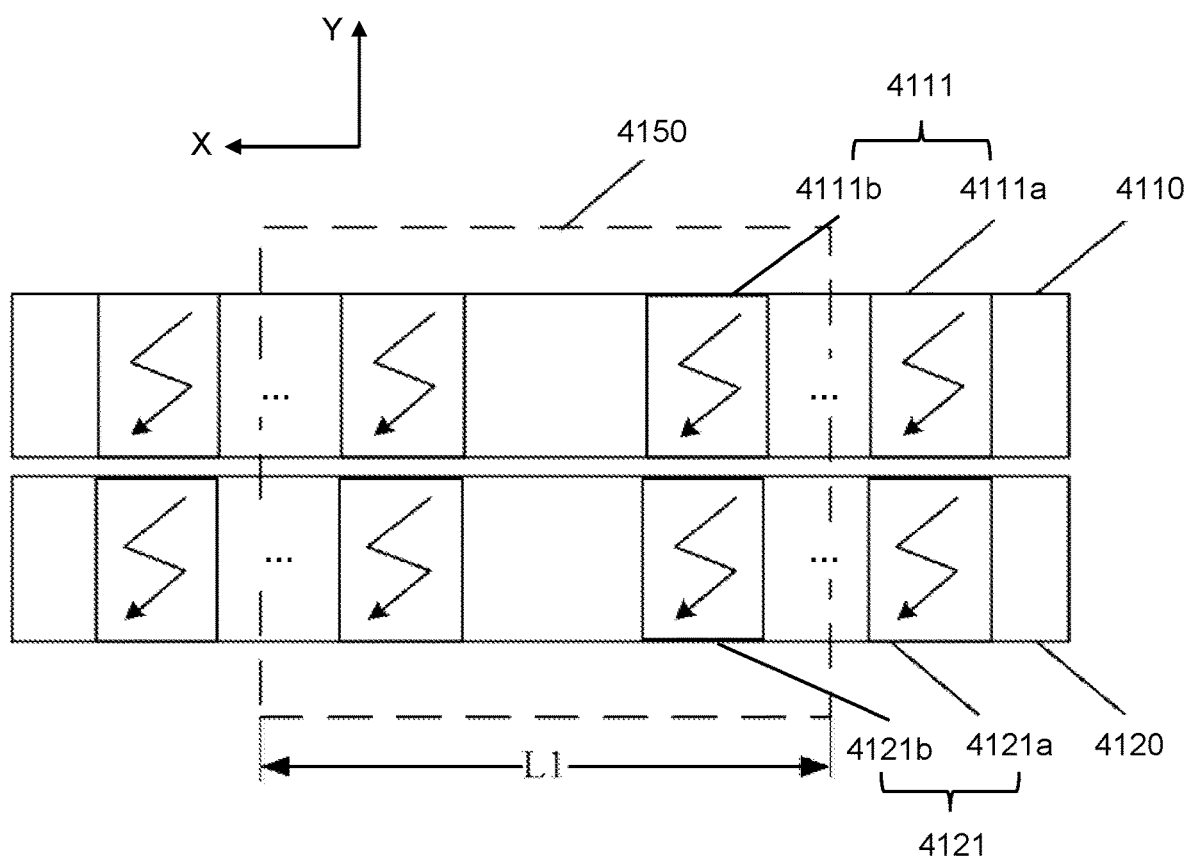
FIG. 4C is an exemplary cross-sectional view of a supporting table and a signal receiver board in the X-Y plane according to some embodiments of the present disclosure.
Figure 4D:
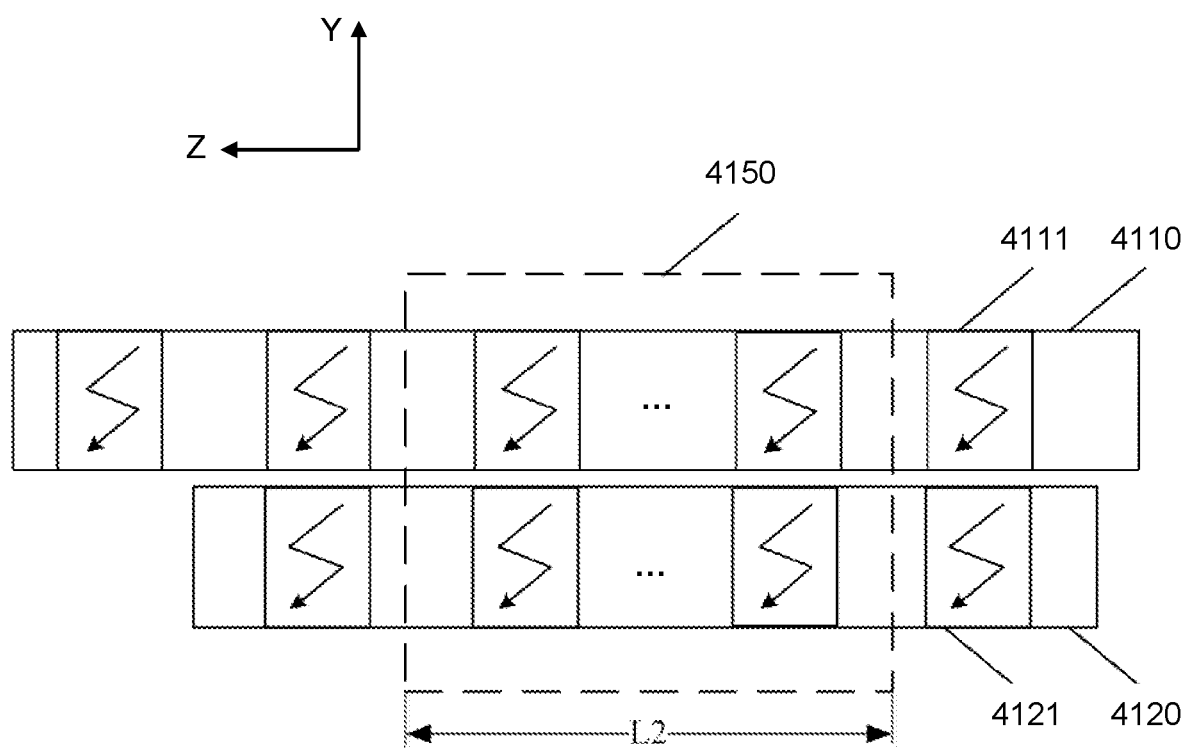
FIG. 4D is an exemplary cross-sectional view of a supporting table and a signal receiver board in the Z-Y plane according to some embodiments of the present disclosure.

FIG. 4C is an exemplary cross-sectional view of a supporting table and a signal receiver board in the X-Y plane according to some embodiments of the present disclosure. FIG. 4D is an exemplary cross-sectional view of a supporting table and a signal receiver board in the Z-Y plane according to some embodiments of the present disclosure. In some embodiments, the plurality of signal transmission ports 4111 may be arranged in one or more rows and/or one or more columns in the supporting table 4110, and the plurality of signal receiving ports 4121 may be arranged in one or more rows and/or one or more columns in the signal receiver board 4120. In some embodiments, a width (in the X-axis direction) of the supporting table 4110 may be the same as a width (in the X-axis direction) of the signal receiver board 4120. In some embodiments, a length (in the Z-axis direction) of the supporting table 4110 may be different from a length (in the Z-axis direction) of the signal receiver board 4120. In some embodiments, the number (or count) of the signal transmission ports 4111 may be greater than the number (or count) of the signal receiving ports 4121, so that signals associated with the portions of the object that are away from each other can be successively received and transmitted without changing a position of the object. In some embodiments, the density of the signal receiving ports 4121 may be greater than the density of the signal transmission ports 4111, so that the signal receiver board 4120 can move by a relatively small distance to make a desired signal transmission port 4111 be coupled with a corresponding signal receiving port 4121. As illustrated in FIGS. 4C-4D, the plurality of signal transmission ports 4111 (e.g., 4111a, 4111b, etc.) may be set (e.g., uniformly distributed) along two long sides (in the Z-axis direction) of the supporting table 4110. The plurality of signal receiving ports 4121 (e.g., 4121a, 4121b, etc.) may be set (e.g., uniformly distributed) along two sides (in the Z-axis direction) of the signal receiver board 4120 corresponding to the two long sides of the supporting table 4110. In some embodiments, at least a portion (e.g., 4111a) of the plurality of signal transmission ports 4111 and at least a portion (e.g., 4121a) of the plurality of signal receiving ports 4121 may be set outside an imaging region 4150 of the MR apparatus 400. In some embodiments, at least a portion (e.g., 4111b) of the plurality of signal transmission ports 4111 and at least a portion (e.g., 4121b) of the plurality of signal receiving ports 4121 may be set inside the imaging region 4150 of the MR apparatus 400. As illustrated in FIG. 4C, a width of the imaging region 4150 (in the X-axis direction) may be represented by L1. As illustrated in FIG. 4D, a depth of the imaging region 4150 (in the Z-axis direction) may be represented by L2.

Figure 4E:
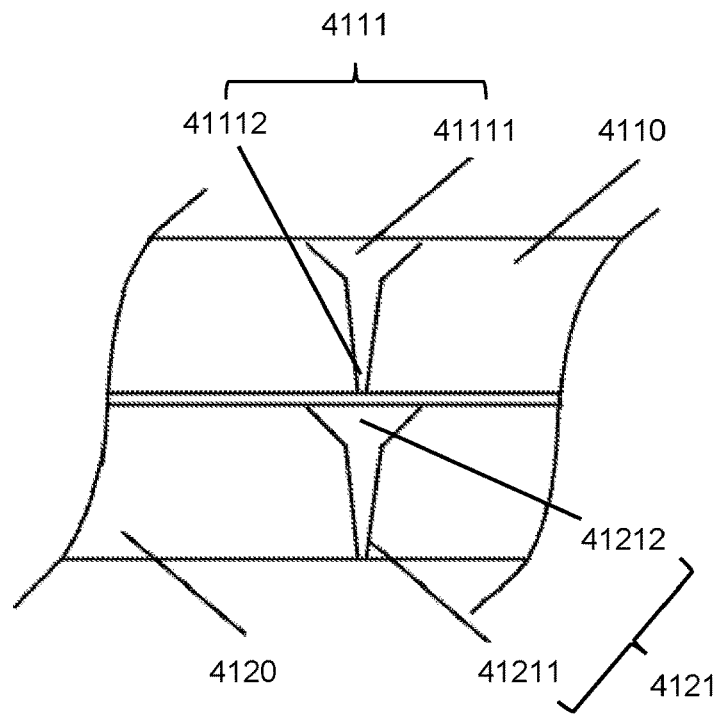
FIG. 4E is a schematic diagram illustrating an exemplary signal transmission port and signal receiving port according to some embodiments of the present disclosure.

FIG. 4E is a schematic diagram illustrating an exemplary signal transmission port and signal receiving port according to some embodiments of the present disclosure. In some embodiments, as illustrated in FIG. 4E, one signal transmission port 4111 in the supporting table 4110 may include a first opening 41111 and a second opening 41112. The first opening 41111 may be further away from the signal receiver board 4120 than the second opening 41112. In some embodiments, still as illustrated in FIG. 4E, one signal receiving port 4121 in the signal receiver board 4120 may include a third opening 41211 and a fourth opening 41212. The third opening 41211 may be further away from the supporting table 4110 than the fourth opening 41212. In some embodiments, still as illustrated in FIG. 4E, a first opening size of the first opening 41111 may be larger than a second opening size of the second opening 41112, and/or a third opening size of the third opening 41211 may be smaller than a fourth opening size of the fourth opening 41212, which can reduce a signal transmission loss between the signal transmission port 4111 and the signal receiving port 4121. In some embodiments, the signal transmission port 4111 set in the supporting table 4110 and the corresponding signal receiving port 4121 set in the signal receiver board 4120 may be configured as a funnel structure.

In the present disclosure, when optical signals enter the signal transmission port 4111 from the first optical fiber 4112, the optical signals may be converged by designing the first opening size of the first opening 41111 and the second opening size of the second opening 41112 of the signal transmission port 4111 (e.g., as illustrated above), thereby reducing a signal loss of the optical signals at the signal transmission port 4111. When the optical signals enter the signal receiving port 4121 from the signal transmission port 4111, the optical signals may be converged by designing the third opening size of the third opening 41211 and the fourth opening size of the fourth opening 41212 of the signal receiving port 4121 (e.g., as illustrated above), thereby reducing the signal loss of the optical signals at the signal receiving port 4121.

Figure 5:
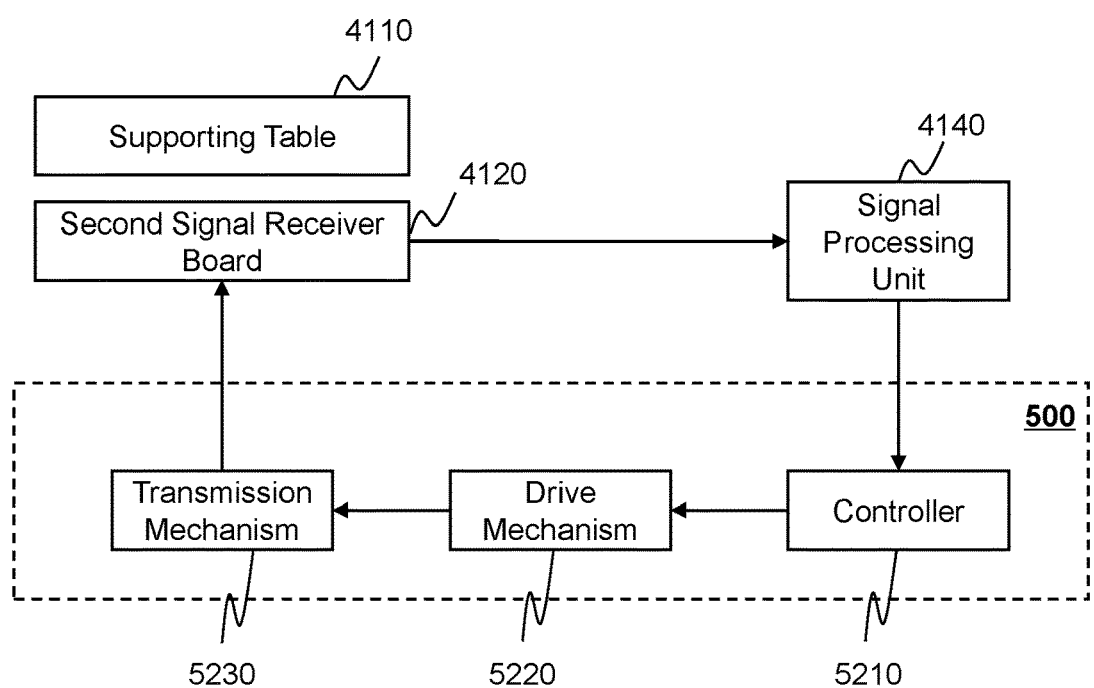
FIG. 5 is a schematic diagram illustrating an exemplary table control module according to some embodiments of the present disclosure.

FIG. 5 a schematic diagram illustrating an exemplary table control module according to some embodiments of the present disclosure. In order to improve the coupling extent between the plurality of signal transmission ports set in the supporting table and corresponding signal receiving ports set in the signal receiver board, a table control module 500 may be set in the MR apparatus 400. The table control module 500 may be configured to control the supporting table and/or the signal receiver board to move. In some embodiments, the table control module 500 may be operably coupled to the supporting table and/or the signal receiver board. In some embodiments, the table control module 500 may be integrated into the supporting table. In some embodiments, the table control module 500 may communicate with the processing device 140, respond to instructions from the processing device 140, and control the supporting table and/or the signal receiver board to move.

For example, the table control module 500 may control the signal receiver board to move back and forth relative to the supporting table along a moving direction of the supporting table (e.g., in the Z-axis direction). As another example, the table control module 500 may control the supporting table to move back and forth relative to the signal receiver board along the moving direction of the supporting table. As a further example, the table control module 500 may control the signal receiver board to move left and/or right relative to the supporting table along a direction perpendicular to the moving direction of the supporting table (e.g., in the X-axis direction). As still a further example, the table control module 500 may control the supporting table to move left and right relative to the signal receiver board along the direction perpendicular to the moving direction of the supporting table.

In some embodiments, as illustrated in FIG. 5, the table control module 500 may include a controller 5210, a drive mechanism 5220, and a transmission mechanism 5230. The controller 5210 may be set between the signal processing unit 4140 and the drive mechanism 5220. The transmission mechanism 5230 may be operably coupled to the drive mechanism 5220. The controller 5210 may be configured to send a control instruction to the drive mechanism 5220 (e.g., when a count of synchronization signal bytes received by the signal processing unit 4140 is different from (e.g., less than) a preset value). As used herein, the synchronization signal bytes may refer to the number (or count) of the bytes that representing the synchronization signal. In some embodiments, the preset value may be a default setting (e.g., an experience value) of the imaging system 100 or may be adjustable according to different situations. The drive mechanism 5220 may be configured to drive, according to the control instruction, the transmission mechanism 5230 to bring the signal receiver board 4120 to move relative to the supporting table 4110 or bring the supporting table 4110 to move relative to the signal receiver board 4120.

Specifically, the supporting table 4110 may be driven to move to a predetermined position to position a target portion of the scanned object in the imaging region. As used herein, the predetermined position may be a default setting of the imaging system 100 or may be adjustable according to different situations. Afterwards, the first signal conversion unit set in the supporting table 4110 may receive MR signals associated with the object and transmit the MR signals to the signal processing unit 4140 via the signal receiver board

4120. In some embodiments, before and/or during the transmission of the MR signals (e.g., once the supporting table 4110 is moved to the predetermined position), the first signal conversion unit may continuously send synchronization signal bytes to the signal processing unit 4140. The signal processing unit 4140 may receive the synchronization signal bytes, and determine the number (or count) of synchronization signal bytes in a preset time period (e.g., in one second, in one minute, etc.). According to the count of received synchronization signal bytes and/or the preset value, the signal processing unit 4140 may determine whether a current signal transmission channel is connected or formed (also referred to as a connection state of the current signal transmission channel). For example, when the count of synchronization signal bytes received by the signal processing unit 4140 is different from (e.g., less than) the preset value, the signal processing unit 4140 may determine that the current signal transmission channel is not connected. As another example, when the count of synchronization signal bytes received by the signal processing unit 4140 is the same as the preset value, the signal processing unit 4140 may determine that the current signal transmission channel is connected. In some embodiments, each signal transmission channel may correspond to a set of synchronization signal bytes. For example, four signal transmission channels may be formed when each of four signal transmission ports is operably coupled to a corresponding signal receiving port, and four first signal conversion units corresponding to the four signal transmission channels may continuously send four sets of synchronization signal bytes to the signal processing unit 4140, respectively. Further, the signal processing unit 4140 may receive the four sets of synchronization signal bytes corresponding to the four signal transmission channels.

Further, the signal processing unit 4140 may transmit the connection state of the current signal transmission channel to the controller 5210. The controller 5210 may generate one or more control instructions according to the connection state. For example, when the current signal transmission channel is not connected, in order to better match the signal receiving port set in the signal receiver board 4120 with the signal transmission port set in the supporting table 4110, and realize complete optical coupling between the first optical fiber and the second optical fiber, the controller 5210 may generate control instruction(s) to drive the signal receiver board 4120 to move. The controller 5210 may transmit the control instruction(s) to the drive mechanism 5220. After receiving the control instruction(s), the drive mechanism 5220 may drive the transmission mechanism 5230 to bring the signal receiver board 4120 to move relative to the supporting table 4110 based on the received control instruction(s). In some embodiments, the table control module 500 may drive the signal receiver board 4120 to move relative to the supporting table 4110 along an axial moving direction (e.g., the Z-axis direction) of the supporting table 4110. In some embodiments, the table control module 500 may drive the supporting table 4110 to move left and/or right relative to the signal receiver board 4120 along a direction perpendicular to the axial moving direction of the supporting table 4110 (e.g., in the X-axis direction). In some embodiments, during the movement of the supporting table 4110 and/or the signal receiver board 4120, the signal processing unit 4140 may continuously receive the synchronization signal bytes, and determine the connection state of the current signal transmission channel. If it is determined that the current signal transmission channel is connected, the table control module 500 may stop moving the supporting table 4110 and/or the signal receiver board 4120. In some embodiments, if there are two or more current signal transmission channels, each current signal transmission channel may be checked as illustrated above. If at least one current signal transmission channel is not connected, the table control module 500 may drive the signal receiver board 4120 to move, until all the current signal transmission channels are determined to be connected, respectively. More descriptions of the control of the movement of the supporting table 4110 and/or the signal receiver board 4120 may be found elsewhere in the present disclosure (e.g., FIGS. 6-7 and descriptions thereof).

In some embodiments, when the supporting table 4110 arrives at the predetermined position, and the signal transmission port is not well aligned with a signal receiving port, it may be indicated that the first optical fiber fails to couple effectivity with the second optical fiber and the current signal transmission channel is not connected. In order to solve the above problem, the table control module 500 configured to control the supporting table 4110 and/or the signal receiver board 4120 to move may be set in the MR apparatus 400, such that the coupling extent between the signal transmission port(s) set in the supporting table and the signal receiving port(s) set in the signal receiver board can be improved, and corresponding signal transmission channel(s) can be formed. Accordingly, the quality of the optical signal(s) transmitted by the signal transmission channel(s) can be improved, and the workflow of scanning the object can be optimized.

Figure 6:
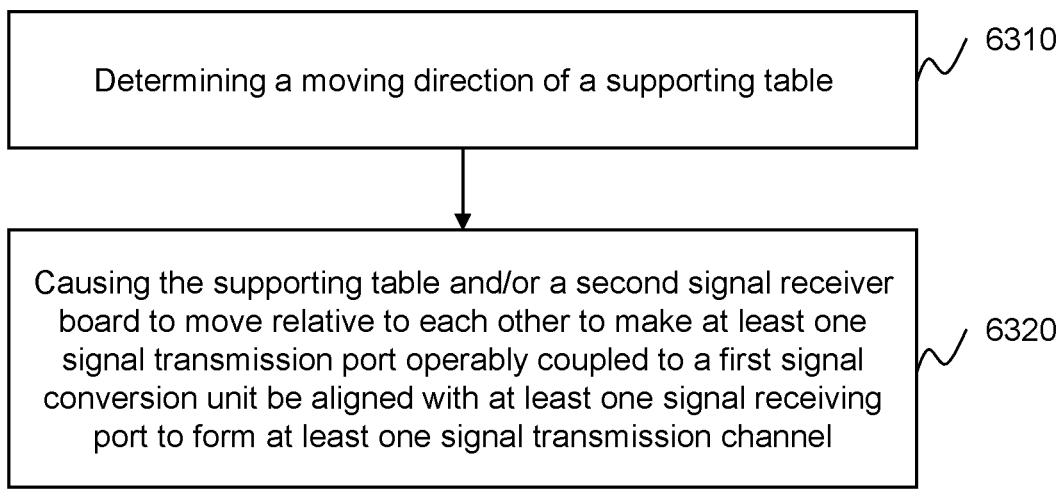
FIG. 6 is a flowchart illustrating an exemplary process for determining a signal transmission channel according to some embodiments of the present disclosure.

FIG. 6 is a flowchart illustrating an exemplary process for determining a signal transmission channel according to some embodiments of the present disclosure. In some embodiments, the process 600 may be implemented in the imaging system 100 illustrated in FIG. 1. For example, the scanner 110 may perform the process 600 to determine one or more signal transmission channels. As another example, the process 600 may be stored in a storage medium (e.g., the storage device 150, or the storage 320 of the processing device 140) as a form of instructions, and can be invoked and/or executed by the processing device 140 (e.g., the processor 310 of the processing device 140). The operations of the illustrated process 600 presented below are intended to be illustrative. In some embodiments, the process 600 may be accomplished with one or more additional operations not described, and/or without one or more of the operations discussed. Additionally, the order in which the operations of the process 600 as illustrated in FIG. 6 and described below is not intended to be limiting.

In some embodiments, the process 600 may be performed by a channel determination module (e.g., the channel determination module 700) including software and/or hardware. In some embodiments, the channel determination module may be part of the scanner 110. In some embodiments, the channel determination module may be set inside the MR apparatus 400 or outside the MR apparatus 400. In some embodiments, the channel determination module may be part of the processing device 140. In some embodiments, a portion of the channel determination module may be integrated into the processing device 140, while another portion of the channel determination module may be integrated into the scanner 110.

In 6310, a moving direction of a supporting table (e.g., the supporting table 4110) may be determined. In some embodiments, the moving direction of the supporting table may be determined by the processing device 140 (e.g., the interface circuits of the processor 210) or the channel determination module 700 (e.g., the determination module 7410). In some embodiments, a table control module (e.g., the table control module 500) may control the table to move to a predetermined position to position a target portion of a scanned object in the imaging region of the MR apparatus 400. In some embodiments, the moving direction of the supporting table may refer to a moving direction from an initial position (e.g., a starting position of the movement) of the supporting table to the predetermined position. In some embodiments, the table control module may record motion status of the supporting table (e.g., a moving direction, a moving speed, an acceleration, a movement distance, a moving time of the supporting table, etc.). In some embodiments, the motion status of the supporting table may be stored in the MR apparatus 400 and/or the storage device (e.g., the storage device 150), and the moving direction of the supporting table may be obtained from the MR apparatus 400 and/or the storage device.

In 6320, the supporting table and/or a signal receiver board (e.g., the signal receiver board 4120) may be caused to move relative to each other. In some embodiments, by moving the supporting table and/or the signal receiver board, at least one signal transmission port (set in the supporting table) that is operably coupled to a first signal conversion unit (e.g., the first signal conversion unit 4130) may be caused to (or made) be aligned with at least one signal receiving port (set in the signal receiver board) to form at least one signal transmission channel. In some embodiments, the supporting table and/or the signal receiver board may be caused to move relative to each other by the processing device 140 (e.g., the processing circuits of the processor 210) or the channel determination module 700 (e.g., the controlling module 7420). More descriptions of the controlling of the movement of the supporting table and/or the signal receiver board may be found elsewhere in the present disclosure (e.g., FIG. 5 and descriptions thereof). In some embodiments, the signal transmission port operably coupled to (e.g., optically connected to) the first signal conversion unit may also be referred to as a "signal transmission port in an active state."

In some embodiments, before a target portion (e.g., an ROI) of an object (e.g., a patient) is scanned by the MR apparatus 400, the first signal conversion unit (e.g., an RF receiving and conversion unit) may be worn on the target portion of the object, and be operably coupled to a signal transmission port via a first optical fiber. In some embodiments, as illustrated in FIG. 4A, the first signal conversion unit may include a plurality of first signal receiving channels (e.g., coil elements). A target channel of the plurality of first signal receiving channels may be configured to receive first signal(s) (e.g., the MR analog signal(s)) associated with the target portion of the object. Further, the first signal(s) may be converted to second signal(s) (e.g., optical signal(s)) by an analog signal processing unit of the first signal conversion unit. In some embodiments, the at least one signal transmission port operably coupled to the first signal conversion unit may correspond to the target channel of the plurality of first signal receiving channels. The target channel of the first signal conversion unit may be connected to the signal transmission port via the first optical fiber.

In some embodiments, the signal transmission port may be operably coupled to the signal receiving port by moving the supporting table and/or the signal receiver board relative to each other, such that the first optical fiber connected to the signal transmission port can be coupled with the second optical fiber connected to the signal receiving port. Further, the second signal(s) may be transmitted to the second optical fiber via the signal transmission port and the signal receiving port operably coupled to the signal transmission port. A signal transmission channel including the first optical fiber, the signal transmission port, the signal receiving port, and the second optical fiber may be formed and configured to transmit the optical signal(s).

In some embodiments, the supporting table may be caused to move relative to the signal receiver board. For example, the supporting table may be caused to move back and forth relative to the signal receiver board along the moving direction of the supporting table. In some embodiments, the signal receiver board may be caused to move relative to the supporting table. For example, the signal receiver board may be caused to move back and forth relative to the supporting table along a moving direction of the supporting table. In some embodiments, the signal receiver board may be caused to move relative to the supporting table in an initial direction parallel to the moving direction of the supporting table. As used herein, the initial direction may be a default setting (e.g., back, forth, right, left) of the imaging system 100 or may be adjustable according to different situations.

In the present disclosure, one or more signal transmission port in active states may be operably coupled to one or more signal receiving ports by determining the moving direction of the supporting table and causing the supporting table and/or the signal receiver board to move relative to each other. Further, the first optical fiber(s) connected to the signal transmission port(s) may be coupled with the second optical fiber(s) connected to the signal receiving port(s), respectively, and signal transmission channel(s) may be formed, thereby reducing an inconvenience of channel determination using a switch matrix circuit, an operation complexity of channel determination, and hardware costs, improving the quality of optical signals transmitted by the channel(s), and optimizing the workflow of scanning the object.

In some embodiments, in order to accurately scan the target portion of the object and improve the quality of optical signals transmitted by the signal transmission channel(s), a count of signal transmission channels that are formed may be detected when the supporting table and/or the signal receiver board are moved. In some embodiments, after the supporting table is moved to the predetermined position, whether a preset count (e.g., with a first preset value) of signal transmission channels are formed may be determined (e.g., by the signal processing unit 4140, the table control module 500, channel determination module, or the processing device 140). Further, the count of signal transmission channels that are formed may be compared with the first preset value. As used herein, the first preset value may be a default setting (e.g., an experience value) of the imaging system 100 or may be adjustable according to different situations. In some embodiments, in response to a determination that the count is less than the first preset value, the signal receiver board may be caused to move in a first direction and/or a second direction until the count of signal transmission channels that are formed is equal to the first preset value. As used herein, the first direction may refer to the moving direction of the supporting table, and the second direction may refer to a direction opposite to the moving direction of the supporting table. In some embodiments, a moving speed of the signal receiver board may be set as a fixed value or an adjustable value (e.g., by an operator or engineer based on experiences).

In some embodiments, the position of the supporting table may be represented by a table code (interchangeably referred to as "couch code") recorded by and/or in the MR apparatus 400, and/or can be read from the MR apparatus 400. In some embodiments, when the target portion of the object is scanned by the MR apparatus 400, a target table code of the supporting table may be determined based on the target portion of the object. In some embodiments, the target table code may correspond to the predetermined position that the supporting table needs to be moved. For example, when the object to be scanned lies in the supporting table, and the supporting table is moved to the predetermined position based on the target table code, the target portion of the object may be positioned in the imaging region of the MR apparatus 400. In some embodiments, when the supporting table reaches the predetermined position, the count of signal transmission channels that are formed may be determined based on the count of synchronization signal bytes received by the signal processing unit 4140. In some embodiments, the count of signal transmission channels that are formed may be compared with one or more preset values to determine whether all desired signal transmission channels are formed.

In some embodiments, a total count of the synchronization signal bytes received from the signal transmission channels may be determined. Alternatively, or additionally, for each of the signal transmission channels, a respective count of received synchronization signal bytes corresponding to each signal transmission channel may be determined. In some embodiments, the total count or the respective count may be compared with a preset value (e.g., a third preset value) to determine whether corresponding signal transmission channel(s) are formed. Specifically, if the total count or the respective count of the received synchronization signal bytes corresponding to the signal transmission channel(s) is equal to the third preset value, the signal transmission channel(s) may be determined to be formed.

In some embodiments, when the count of signal transmission channels that are formed is less than the first preset value (i.e., at least one signal transmission channel is not formed), a controller (e.g., the controller 5210) may generate a control instruction and transmit the control instruction to a drive mechanism (e.g., the drive mechanism 5220). Further, the drive mechanism may drive a transmission mechanism (e.g., the transmission mechanism 5230) to bring the signal receiver board to move relative to the supporting table along the first direction and/or the second direction until the count of signal transmission channels that are formed is equal to the first preset value.

In some embodiments, before the count of signal transmission channels that are formed is equal to the first preset value, in order to improve the efficiency of determining the signal transmission channel(s) and avoid an invalid movement of the signal receiver board, a movement distance of the signal receiver board may be determined. In some embodiments, the movement distance may be compared with a second preset value. As used herein, the second preset value may be a default setting of the imaging system 100 or may be adjustable according to different situations. For example, the second preset value may be a preset multiple of a length of a long side edge of the supporting table, in which the preset multiple may be, e.g., 2 or a value larger than 2. In response to a determination that the movement distance exceeds the second preset value and the count of signal transmission channels that are formed is less than the first preset value, the operation of moving the signal receiver board may be stopped, and/or an alarm may be provided.

In some embodiments, if the movement distance of the signal receiver board exceeds the second preset value, and the count of signal transmission channels that are formed is still less than the first preset value, it may be indicated that a connection between the first signal conversion unit and the signal transmission port is abnormal or a connection between the signal receiving port and the signal processing unit is abnormal. Accordingly, the signal transmission channel(s) cannot be formed by moving the signal receiver board. In order to avoid the invalid movement of the signal receiver board and timely notify the operator to troubleshoot the signal transmission channel(s), the signal receiver board can be forcibly stopped and the alarm can be provided.

In some embodiments, after each movement of the signal receiver board, inertia existing during the movement may cause a distance deviation between an actual position and a theoretical (or recorded) position of the signal receiver board. In order to effectively compensate for the distance deviation, and improve the efficiency of determining the signal transmission channel(s) and the quality of optical signals transmitted by the signal transmission channel(s), the signal receiver board may be caused to move back by a preset distance (e.g., along a direction opposite to a moving direction of the signal receiver board before the signal receiver board stops). As used herein, the preset distance may be a default setting of the imaging system 100 or may be adjustable according to different situations. For example, the preset distance may be determined by a technician based on a plurality of tests.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 7:
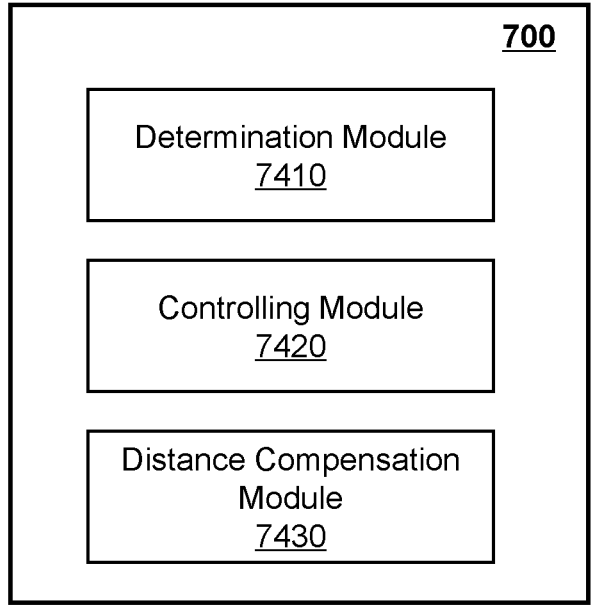
FIG. 7 is a schematic block diagram illustrating an exemplary channel determination module according to some embodiments of the present disclosure.

FIG. 7 is a schematic block diagram illustrating an exemplary channel determination module according to some embodiments of the present disclosure. The modules in the channel determination module 700 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined as a single module, and any one of the modules may be divided into two or more units.

In some embodiments, the channel determination module 700 may be set in the MR apparatus 400. In some embodiments, the channel determination module 700 may include software and/or hardware. In some embodiments, the channel determination module 700 may perform the process 600 to determine signal transmission channel(s).

As illustrated in FIG. 7, the channel determination module 700 may include a determination module 7410 (also referred to as an "obtaining module") and a controlling module 7420. The determination module 7410 may be configured to determine a moving direction of the supporting table. The controlling module 7420 may be configured to cause the supporting table or a signal receiver board to move relative to each other to make at least one signal transmission port operably coupled to a first signal conversion unit to be aligned with at least one signal receiving port to form a signal transmission channel.

In the present disclosure, the signal transmission port(s) in active states may be operably coupled to the signal receiving port(s) by determining a moving direction of the supporting table and causing the supporting table or the signal receiver board to move relative to each other. Further, the first optical fiber connected to the signal transmission port may be coupled with the second optical fiber connected to the signal receiving port to form the signal transmission channel, thereby reducing an inconvenience of channel determination caused by using a switch matrix circuit, an operation complexity of channel determination, and hardware costs, improving the quality of optical signals transmitted by the signal transmission channel(s), and optimizing the workflow of scanning the object.

In some embodiments, the controlling module 7420 may be further configured to cause the signal receiver board to move relative to the supporting table in an initial direction parallel to the moving direction of the supporting table. In some embodiments, the initial direction may be the same as the moving direction of the supporting table. In some embodiments, the initial direction may be opposite to the moving direction of the supporting table.

In some embodiments, upon the supporting table and/or the signal receiver board being moved to a predetermined position, the controlling module 7420 may detect a count of signal transmission channels that are formed and compare the count with a first preset value. In response to a determination that the count is less than the first preset value, the controlling module 7420 may cause the signal receiver board to move in a first direction and/or a second direction until the count of signal transmission channels that are formed is equal to the first preset value. In some embodiments, the first direction may refer to the moving direction of the supporting table, and the second direction may refer to a direction opposite to the moving direction of the supporting table.

In some embodiments, before the count of signal transmission channels that are formed is equal to the first preset value, the controlling module 7420 may determine a movement distance of the signal receiver board and compare the movement distance with a second preset value. In response to a determination that the movement distance exceeds the second preset value and the count is less than the first preset value, the controlling module 7420 may stop moving the signal receiver board and provide an alarm.

In some embodiments, the channel determination module 700 may further include a distance compensation module 7430. The distance compensation module 7430 may be configured to cause the signal receiver board to move by a preset distance along a direction opposite to the moving direction of the signal receiver board (e.g., the moving direction of the signal receiver board before the signal receiver board stops).

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the controlling module 7420 and the distance compensation module 7430 may be combined as a single module configured to both cause the supporting table and/or the signal receiver board to move relative to each other and cause the signal receiver board to move by a preset distance along a direction opposite to the moving direction of the signal receiver board. As another example, the channel determination module 700 may further include a storage module (not shown in FIG. 7). The storage module may be configured to store data generated during any process performed by any component of the channel determination module 700. As a further example, each component of the channel determination module 700 may include a storage device. Additionally, or alternatively, the components of the channel determination module 700 may share a common storage device.

The present disclosure may also provide a computer readable storage medium storing a computer program thereon. When executing by at least one processor, the executable instructions may direct the at least one processor to perform a process (e.g., process 600) described elsewhere in the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

What is claimed is:

1. A system for scanning an object, comprising:
a supporting table configured to support the object, a plurality of signal transmission ports being disposed on the supporting table;
a first signal conversion unit configured to receive one or more first signals associated with the object and convert the one or more first signals into one or more second signals; and
a signal receiver board configured to receive the one or more second signals, a plurality of signal receiving ports being disposed on the signal receiver board, wherein
the first signal conversion unit includes a plurality of first signal receiving channels, each channel of the plurality of first signal receiving channels being configured to receive a first signal associated with a portion of the object and transmit a second signal corresponding to the first signal to at least one signal transmission port of the plurality of signal transmission ports, and
the supporting table and the signal receiver board are configured to move relative to each other to cause the signal receiver board to receive, via at least one signal receiving port of the plurality of signal receiving ports, at least one second signal corresponding to at least one first signal received by at least one target channel of the plurality of first signal receiving channels.

2. The system of claim 1, further comprising a signal processing unit, wherein
the signal receiver board is further configured to transmit the one or more second signals to the signal processing unit, and
the signal processing unit is configured to receive the one or more second signals and process the one or more second signals.

3. The system of claim 1, wherein the signal receiver board is positioned underneath the supporting table.

4. The system of claim 1, wherein the supporting table and the second signal receiver board are configured to move relative to each other to cause at least one signal transmission port of the plurality of signal transmission ports to be operably coupled to at least one signal receiving port of the plurality of signal receiving ports, such that the at least one second signal is received by the second signal receiver board.

5. The system of claim 1, wherein the one or more second signals are one or more optical signals, and the first signal conversion unit is operably coupled to at least one signal transmission port of the plurality of signal transmission ports via a first optical fiber.

6. The system of claim 1, further comprising a signal processing unit configured to process the one or more second signals, wherein
the signal processing unit is operably coupled to at least one signal receiving port of the plurality of signal receiving ports via a second optical fiber.

7. The system of claim 6, further comprising:
a table control module configured to control the supporting table or the signal receiver board to move.

8. The system of claim 7, wherein
the table control module includes a controller, a drive mechanism, and a transmission mechanism;
the controller is set between the signal processing unit and the drive mechanism;
the transmission mechanism is operably connected to the drive mechanism;
the controller is configured to send, when a count of synchronization signal bytes received by the signal processing unit is different from a preset value, a control instruction to the drive mechanism; and
the drive mechanism is configured to drive, based on the control instruction, the transmission mechanism to bring the signal receiver board to move relative to the supporting table, or bring the supporting table to move relative to the signal receiver board.

9. The system of claim 1, wherein at least a portion of the plurality of signal transmission ports are set close to a long side edge of the supporting table, or the plurality of signal transmission ports are set along a long axis direction of the supporting table.

10. The system of claim 9, wherein at least a portion of the plurality of signal receiving ports are set close to a side edge of the signal receiver board, the side edge of the signal receiver board corresponding to the long side edge of the supporting table.

11. The system of claim 10, wherein the at least a portion of the plurality of signal transmission ports are uniformly distributed, and the at least a portion of the plurality of signal receiving ports are uniformly distributed.

12. The system of claim 11, wherein a first distance between two adjacent signal transmission ports of the at least a portion of the plurality of signal transmission ports is the same as a second distance between two adjacent signal receiving ports of the at least a portion of the plurality of signal receiving ports.

13. The system of claim 1, wherein the one or more second signals are one or more optical signals, and a signal transmission channel configured to transmit an optical signal of the one or more optical signals is formed when one of the plurality of signal transmission ports is operably coupled to one of the plurality of signal receiving ports.

14. The system of claim 1, wherein
at least one of the plurality of signal transmission ports includes a first opening and a second opening;
the first opening is further away from the signal receiver board than the second opening; and
a first opening size of the first opening is larger than a second opening size of the second opening.

15. The system of claim 1, wherein
at least one of the plurality of signal receiving ports includes a third opening and a fourth opening;
the third opening is further away from the supporting table than the fourth opening; and
a third opening size of the third opening is smaller than a fourth opening size of the fourth opening.

16. The system of claim 1, wherein
the system is a magnetic resonance (MR) system, and the one or more first signals are one or more MR analog signals;
the first signal conversion unit includes a coil element and an analog signal processing unit;
the coil element is operably coupled to the analog signal processing unit, and is configured to receive the one or more MR analog signals; and
the analog signal processing unit is operably coupled to at least one of the plurality of signal transmission ports via a first optical fiber, and is configured to receive the one or more MR analog signals and convert the one or more MR analog signals to one or more optical signals.

17. The system of claim 16, wherein the analog signal processing unit includes:
an analog-to-digital conversion circuit operably coupled to the coil element, and configured to receive the one or more MR analog signals and convert the one or more MR analog signals to one or more MR digital signals; and
a photoelectric conversion circuit set between analog-to-digital conversion circuit and the plurality of signal transmission ports, and configured to convert the one or more MR digital signals to the one or more optical signals, and transmit the one or more optical signals to the at least one of the plurality of signal transmission ports via the first optical fiber.

18. A magnetic resonance (MR) apparatus, comprising:
a supporting table;
a first signal conversion unit;
a signal receiver board; and
a signal processing unit,
wherein
a plurality of signal transmission ports are disposed on the supporting table,
a plurality of signal receiving ports are disposed on the signal receiver board and operably coupled to the plurality of signal transmission ports,
the signal receiver board is positioned underneath the supporting table,
the supporting table and the signal receiver board are configured to move relative to each other to cause at least one signal transmission port of the plurality of signal transmission ports to be aligned with at least one signal receiving port of the plurality of signal receiving ports,
the first signal conversion unit is operably coupled to the at least one signal transmission port via a first optical fiber, and is configured to receive magnetic resonance (MR) analog signals associated with an object, and convert the MR analog signals to optical signals, and
the signal processing unit is operably coupled to the at least one signal receiving port via a second optical fiber, and is configured to receive the optical signals and process the optical signals.

19. A method implemented on at least one machine each of which has at least one processor and at least one storage device for determining a signal transmission channel in a system, the method comprising:
determining a moving direction of a supporting table of the system; and
causing the supporting table or a signal receiver board of the system to move relative to each other to make at least one signal transmission port disposed on the supporting table and operably coupled to a first signal conversion unit of the system be aligned with at least one signal receiving port disposed on the signal receiver board to form the signal transmission channel.

\* \* \* \* \*